(12) United States Patent
Buchholz et al.

(10) Patent No.: US 9,719,109 B2
(45) Date of Patent: Aug. 1, 2017

(54) PROTEIN WITH RECOMBINASE ACTIVITY FOR SITE-SPECIFIC DNA-RECOMBINATION

(71) Applicant: Technische Universität Dresden, Dresden (DE)

(72) Inventors: Frank Buchholz, Dresden (DE); Madina Karimova, Dresden (DE)

(73) Assignee: Technische Universitat Dresden, Dresden (DE)

( * ) Notice: Subject to any disclaimer, the term of this patent is extended or adjusted under 35 U.S.C. 154(b) by 0 days.

(21) Appl. No.: 15/216,215

(22) Filed: Jul. 21, 2016

(65) Prior Publication Data

US 2017/0016029 A1    Jan. 19, 2017

Related U.S. Application Data

(63) Continuation of application No. 14/416,997, filed as application No. PCT/EP2013/065417 on Jul. 22, 2013, now Pat. No. 9,428,754.

(30) Foreign Application Priority Data

Jul. 24, 2012 (EP) .................... 12177608

(51) Int. Cl.
| | |
|---|---|
| *C12N 15/87* | (2006.01) |
| *C12N 15/52* | (2006.01) |
| *C12N 15/90* | (2006.01) |
| *C12N 9/12* | (2006.01) |
| *C12N 15/85* | (2006.01) |
| *C07H 21/04* | (2006.01) |
| *C12N 15/55* | (2006.01) |
| *C12N 15/63* | (2006.01) |
| *C12N 15/66* | (2006.01) |

(52) U.S. Cl.
CPC ............. *C12N 15/907* (2013.01); *C12N 9/12* (2013.01); *C12N 9/1241* (2013.01); *C12N 15/52* (2013.01); *C12N 15/85* (2013.01); *C12N 15/902* (2013.01); *C12Y 207/07* (2013.01); *C12N 2320/33* (2013.01)

(58) Field of Classification Search
None
See application file for complete search history.

(56) References Cited

U.S. PATENT DOCUMENTS

| | | |
|---|---|---|
| 7,422,889 B2 | 9/2008 | Sauer et al. |
| 7,915,037 B2 | 3/2011 | Sauer et al. |
| 2006/0014264 A1 | 1/2006 | Sauer et al. |

FOREIGN PATENT DOCUMENTS

| | | |
|---|---|---|
| DE | 102 07 313 A1 | 9/2003 |
| EP | 0 200 009 B1 | 1/1991 |
| EP | 2 690 177 B1 | 12/2014 |
| WO | WO 2010/143606 A1 | 12/2010 |

OTHER PUBLICATIONS

Buchholz, F., and Bishop, J.M., "IoxP-Directed Cloning: Use of Cre Recombinase as a Universal Restriction Enzyme," *BioTechniques* 31(4):906-918, Informa BioSciences, United States (2001).
Buchholz, F., and Stewart, A.F., "Alteration of Cre recombinase site specificity by substrate-linked protein evolution," *Nature Biotechnology* 19:1047-1052, Nature Publishing Group, United Kingdom (2001).
Chung, Y., et al., "Human Embryonic Stem Cell Lines Generated without Embryo Destruction," *Cell Stem Cell* 2:113-117, Elsevier Inc., Netherlands (2008).
Database Geneseq [Online]: accession No. AEF42147, "Cre recombinase homolog 17938604 SEQ ID No. 13," XP002713208, Mar. 23, 2006, retrieved from EBI accession No. GSP:AEF42147.
Database UniProt [Online]: accession No. C7CN12, "SubName: Full=Putative Phage integrase (Cre-like);" XP002713209, Sep. 22, 2009, retrieved from EBI accession No. UNIPORT:C7CN12.
Kimes, N.E., et al., "Temperature regulation of virulence factors in the pathogen *Vibrio coralliilyticus*," *The ISME Journal* 6:835-846, International Society for Microbial Ecology, Netherlands (2012).
Lin, G., et al., "A highly homozygous and parthenogenetic human embryonic stem cell line derived from a one-pronuclear oocyte following in vitro fertilization procedure," *Cell Research* 17:999-1007, Nature Publishing Group, United Kingdom (2007).
Mai, Q., et al., "Derivation of human embryonic stem cell lines from parthenogenetic blastocysts," *Cell Research* 17:1008-1019, Nature Publishing Group, United Kingdom (2007).
Suzuki, E., and Nakayama, M., "VCre/VloxP and SCre/SloxP: new site-specific recombination systems for genome engineering," *Nucleic Acids Research* 39(8):e49, Oxford University Press, United Kingdom (2011).
Vuilleumier, S., et al.,"*Methylobacterium* Genome Sequences: A Reference Blueprint to Investigate Microbial Metabolism of Cl Compounds from Natural and Industrial Sources," *PLOS ONE* 4(5):e5584, Public Library of Science, United States (2009).
International Search Report for International Patent Application No. PCT/EP2013/065417, filed Jul. 22, 2013, mailed on Oct. 18, 2013, European Patent Office, The Hague, Netherlands.

*Primary Examiner* — Nancy J Leith
(74) *Attorney, Agent, or Firm* — Sterne, Kessler, Goldstein & Fox P.L.L.C.

(57) ABSTRACT

The invention relates to the use of a protein with recombinase activity to catalyze a site-specific DNA recombination and a method for producing a site-specific DNA recombination. The invention is applicable alone or in combination with other recombinase systems for genetic manipulation, for example in medical research. The objective of the invention is solved by the use of a protein with recombinase activity to catalyze a site-specific DNA recombination at, preferably at two, recognition sites that are identical or reverse complementary to each other. The invention also includes a method for producing a site-specific DNA recombination comprising the steps of a) providing a cell comprising at least two recognition sites that are identical or reverse complementary to each other; and b) contacting a protein with recombinase activity with the recognition sites, thereby producing the site-specific DNA-recombination.

8 Claims, 13 Drawing Sheets

```
Vika  MTDLTPFPPLEHLEPDEFADLVRKAIKRDPQAGAHPAIQSAISHFQDEFVRRQGEWQPATLQRLRNAWNVFVRWC  75
Cre   ---------------MSNLLTVHQNLPALPVDATSDEVRKNLMDMFRDRQAFSFHTWKMLLSVCRSWAAWC  56

Vika  THQGIPALPARHQDVERYLIERRN-ELHRNTLKVHLWAIGKTHVISGLPNPCAHRYVKAQMAQITHQKVRERERI  149
Cre   KLNNRKWFPAEPEDVRDYLLYLQARGLAVKTIQQHLGQLNMLHRRSGLPRPSDSNAVSLVMRRIRKENVDAGERA  131

Vika  EQAPAFRESDLDRLTELWSATRSVTQQRDLMIVSLAYETLLRKNNLEQMKVGDIEFCQDGSALITIPFSKTNHSG  224
Cre   KQALAFERTDFDQVRSLMENSDRCQDIRNLAFLGIAYNTLLRIAETARIRVKDISRTDGGRMLIHIGRTKTLVST  206

Vika  RDDVRWISPQVANQVHAYLQLPNIDADPQCFLLQRVKRSGKALNPESHNTLNGHHPVSEKLISRVFERAWRALNH  299
Cre   AGVEKALSLGVTKLVERWISVSGVADDPNNYLFCRVRKNGVAA------PSATSQLSTRALEGIFEATHRLIYG  274

Vika  ETG------PRYTGHSARVGAAQDLLQEGYSTLQVMQAGGWSSEKMVLRYGRHLHAHTSAMAQKRQR  361
Cre   AKDDSGQRYLAWSGHSARVGAARDMARAGVSIPEIMQAGGWTNVNIVMNYIRNLDSETGAMVRLLEDGD  343
```

Fig. 1

```
loxP    ATAACTTCGTATAGCATACATTATACGAAGTTAT 34
rox     -TAACTTTAAATAATTGGCATTATTTAAAGTTA- 32
vloxP   TCAATTTCCGAGAATGACAGTTCTCAGAAATTGA 34
vox     AATAGGTCTGAGAACGCCCATTCTCAGACGTATT 34
                    *  *    *  **  *   *   *
```
Fig. 3
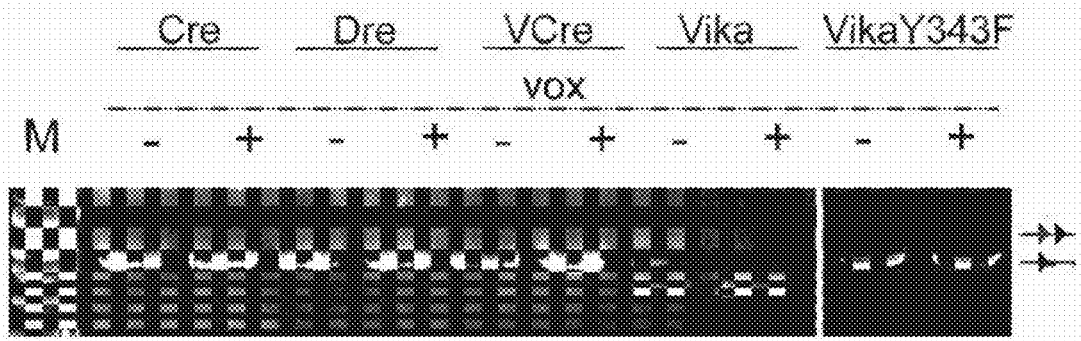
Fig. 4A
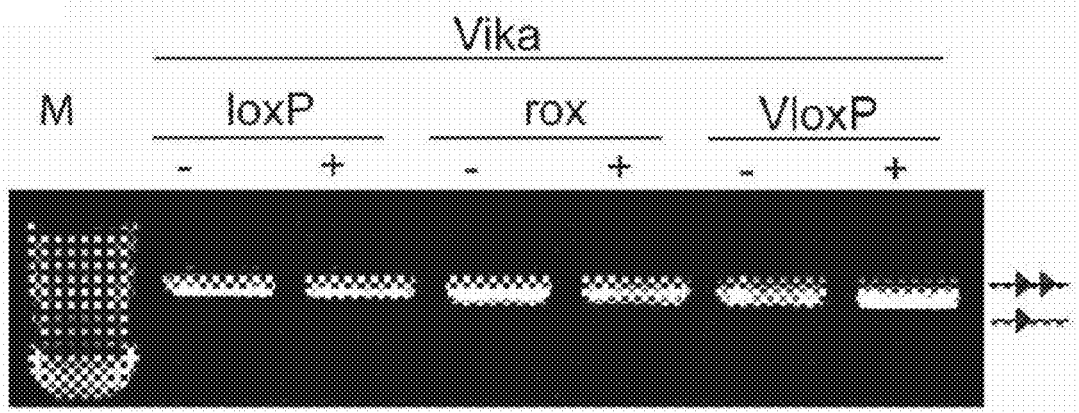
Fig. 4B

SEQUENCE LISTING

<160> NUMBER OF SEQ ID NOS: 38

<210> SEQ ID NO 1
<211> LENGTH: 361
<212> TYPE: PRT
<213> ORGANISM: Vibrio coralliilyticus

<400> SEQUENCE: 1

Met Thr Asp Leu Thr Pro Phe Pro Pro Leu Glu His Leu Glu Pro Asp
1               5                   10                  15

Glu Phe Ala Asp Leu Val Arg Lys Ala Ile Lys Arg Asp Pro Gln Ala
            20                  25                  30

Gly Ala His Pro Ala Ile Gln Ser Ala Ile Ser His Phe Gln Asp Glu
        35                  40                  45

Phe Val Arg Arg Gln Gly Glu Trp Gln Pro Ala Thr Leu Gln Arg Leu
    50                  55                  60

Arg Asn Ala Trp Asn Val Phe Val Arg Trp Cys Thr His Gln Gly Ile
65                  70                  75                  80

Pro Ala Leu Pro Ala Arg His Gln Asp Val Glu Arg Tyr Leu Ile Glu
                85                  90                  95

Arg Arg Asn Glu Leu His Arg Asn Thr Leu Lys Val His Leu Trp Ala
            100                 105                 110

Ile Gly Lys Thr His Val Ile Ser Gly Leu Pro Asn Pro Cys Ala His
        115                 120                 125

Arg Tyr Val Lys Ala Gln Met Ala Gln Ile Thr His Gln Lys Val Arg
    130                 135                 140

Glu Arg Glu Arg Ile Glu Gln Ala Pro Ala Phe Arg Glu Ser Asp Leu
145                 150                 155                 160

Asp Arg Leu Thr Glu Leu Trp Ser Ala Thr Arg Ser Val Thr Gln Gln

```
                        165                 170                 175
Arg Asp Leu Met Ile Val Ser Leu Ala Tyr Glu Thr Leu Leu Arg Lys
            180                 185                 190

Asn Asn Leu Glu Gln Met Lys Val Gly Asp Ile Glu Phe Cys Gln Asp
        195                 200                 205

Gly Ser Ala Leu Ile Thr Ile Pro Phe Ser Lys Thr Asn His Ser Gly
        210                 215                 220

Arg Asp Asp Val Arg Trp Ile Ser Pro Gln Val Ala Asn Gln Val His
225                 230                 235                 240

Ala Tyr Leu Gln Leu Pro Asn Ile Asp Ala Asp Pro Gln Cys Phe Leu
            245                 250                 255

Leu Gln Arg Val Lys Arg Ser Gly Lys Ala Leu Asn Pro Glu Ser His
            260                 265                 270

Asn Thr Leu Asn Gly His His Pro Val Ser Glu Lys Leu Ile Ser Arg
        275                 280                 285

Val Phe Glu Arg Ala Trp Arg Ala Leu Asn His Glu Thr Gly Pro Arg
    290                 295                 300

Tyr Thr Gly His Ser Ala Arg Val Gly Ala Ala Gln Asp Leu Leu Gln
305                 310                 315                 320

Glu Gly Tyr Ser Thr Leu Gln Val Met Gln Ala Gly Gly Trp Ser Ser
            325                 330                 335

Glu Lys Met Val Leu Arg Tyr Gly Arg His Leu His Ala His Thr Ser
            340                 345                 350

Ala Met Ala Gln Lys Arg Arg Gln Arg
        355                 360

<210> SEQ ID NO 2
<211> LENGTH: 34
<212> TYPE: DNA
<213> ORGANISM: Vibrio coralliilyticus

<400> SEQUENCE: 2
aataggtctg agaacgccca ttctcagacg tatt                               34

<210> SEQ ID NO 3
<211> LENGTH: 1083
<212> TYPE: DNA
<213> ORGANISM: Vibrio coralliilyticus

<400> SEQUENCE: 3
atgaccgacc tgaccccctt cccccccctg gaacacctgg aacccgacga gttcgccgac    60
ctggtccgca aggccatcaa gagggatccc caggctggcg cccaccctgc catccagagc   120
gccatcagcc acttccagga cgagttcgtg cggcggcagg gagagtggca gccagctaca   180
ctgcagcggc tgcggaacgc ctggaacgtg ttcgtgcggt ggtgcacccc ccagggcatt   240
cccgccctgc cgccagaca ccaggacgtg gaaagatacc tgatcgagcg gcggaacgag   300
ctgcaccgga cacccctgaa ggtgcacctg tgggccatcg gcaagaccca cgtgatcagc   360
ggcctgccca cccctgcgc ccacagatac gtgaaagccc agatggccca gatcacccac   420
cagaaagtgc gcgagagaga gcggatcgag caggcccctg ccttcagaga gagcgacctg   480
gaccggctga ccgagctgtg gtccgccacc agaagcgtga cccagcagcg ggacctgatg   540
atcgtgtccc tggcctacga gacactgctg cggaagaaca acctggaaca gatgaaagtg   600
ggcgacatcg agttctgcca ggacggcagc gccctgatca ccatcccctt cagcaagacc   660
aaccacagcg gcagggacga cgtgcggtgg atcagccccc aggtggccaa ccaggtgcac   720
```

-continued

```
gcctacctgc agctgcccaa catcgacgcc gaccccagt gcttcctgct gcagagagtg    780
aagcggagcg gcaaggccct gaaccccgag agccacaata ccctgaacgg ccaccacccc    840
gtgtccgaga agctgatcag ccgggtgttc agcgggcct ggcgggctct gaatcacgag    900
acaggcccca gatacaccgg ccacagcgcc agagtgggag ccgcccagga tctgctgcag    960
gaaggctaca gcaccctgca ggtcatgcag gctggcggct ggtccagcga agatggtg    1020 ctgagatacg ccggcatct gcacgcccac accagcgcca tggcccagaa gcggagacag    1080
cgg                                                                  1083
```

<210> SEQ ID NO 4
<211> LENGTH: 343
<212> TYPE: PRT
<213> ORGANISM: Bacteriophage P1

<400> SEQUENCE: 4

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300
```

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
            325                 330                 335

Arg Leu Leu Glu Asp Gly Asp
            340

<210> SEQ ID NO 5
<211> LENGTH: 34
<212> TYPE: DNA
<213> ORGANISM: Bacteriophage P1

<400> SEQUENCE: 5
ataacttcgt atagcataca ttatacgaag ttat                              34

<210> SEQ ID NO 6
<211> LENGTH: 423
<212> TYPE: PRT
<213> ORGANISM: Saccharomyces cerevisiae

<400> SEQUENCE: 6

Met Pro Gln Phe Gly Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Leu Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
            260                 265                 270

```
Gln Leu Leu Lys Asp Asn Leu Val Arg Ser Tyr Asn Lys Ala Leu Lys
            275                 280                 285

Lys Asn Ala Pro Tyr Ser Ile Phe Ala Ile Lys Asn Gly Pro Lys Ser
        290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
        355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
            420

<210> SEQ ID NO 7
<211> LENGTH: 34
<212> TYPE: DNA
<213> ORGANISM: Saccharomyces cerevisiae

<400> SEQUENCE: 7
gaagttccta tactttctag agaataggaa cttc                               34

<210> SEQ ID NO 8
<211> LENGTH: 342
<212> TYPE: PRT
<213> ORGANISM: Enterobacteria phage D6

<400> SEQUENCE: 8

Met Ser Glu Leu Ile Ile Ser Gly Ser Ser Gly Gly Phe Leu Arg Asn
1               5                   10                  15

Ile Gly Lys Glu Tyr Gln Glu Ala Ala Glu Asn Phe Met Arg Phe Met
            20                  25                  30

Asn Asp Gln Gly Ala Tyr Ala Pro Asn Thr Leu Arg Asp Leu Arg Leu
        35                  40                  45

Val Phe His Ser Trp Ala Arg Trp Cys His Ala Arg Gln Leu Ala Trp
    50                  55                  60

Phe Pro Ile Ser Pro Glu Met Ala Arg Glu Tyr Phe Leu Gln Leu His
65                  70                  75                  80

Asp Ala Asp Leu Ala Ser Thr Thr Ile Asp Lys His Tyr Ala Met Leu
                85                  90                  95

Asn Met Leu Leu Ser His Cys Gly Leu Pro Pro Leu Ser Asp Asp Lys
            100                 105                 110

Ser Val Ser Leu Ala Met Arg Arg Ile Arg Arg Glu Ala Ala Thr Glu
        115                 120                 125

Lys Gly Glu Arg Thr Gly Gln Ala Ile Pro Leu Arg Trp Asp Asp Leu
    130                 135                 140

Lys Leu Leu Asp Val Leu Leu Ser Arg Ser Glu Arg Leu Val Asp Leu
145                 150                 155                 160

Arg Asn Arg Ala Phe Leu Phe Val Ala Tyr Asn Thr Leu Met Arg Met
```

```
                   165                 170                 175
Ser Glu Ile Ser Arg Ile Arg Val Gly Asp Leu Asp Gln Thr Gly Asp
            180                 185                 190

Thr Val Thr Leu His Ile Ser His Thr Lys Thr Ile Thr Ala Ala
        195                 200                 205

Gly Leu Asp Lys Val Leu Ser Arg Thr Thr Ala Val Leu Asn Asp
    210                 215                 220

Trp Leu Asp Val Ser Gly Leu Arg Glu His Pro Asp Ala Val Leu Phe
225                 230                 235                 240

Pro Pro Ile His Arg Ser Asn Lys Ala Arg Ile Thr Thr Pro Leu
            245                 250                 255

Thr Ala Pro Ala Met Glu Lys Ile Phe Ser Asp Ala Trp Val Leu Leu
        260                 265                 270

Asn Lys Arg Asp Ala Thr Pro Asn Lys Gly Arg Tyr Arg Thr Trp Thr
    275                 280                 285

Gly His Ser Ala Arg Val Gly Ala Ala Ile Asp Met Ala Glu Lys Gln
    290                 295                 300

Val Ser Met Val Glu Ile Met Gln Glu Gly Thr Trp Lys Lys Pro Glu
305                 310                 315                 320

Thr Leu Met Arg Tyr Leu Arg Arg Gly Gly Val Ser Val Gly Ala Asn
                325                 330                 335

Ser Arg Leu Met Asp Ser
            340

<210> SEQ ID NO 9
<211> LENGTH: 32
<212> TYPE: DNA
<213> ORGANISM: Eubacterium xylanophilum

<400> SEQUENCE: 9
taactttaaa taattggcat tatttaaagt ta                                32

<210> SEQ ID NO 10
<211> LENGTH: 380
<212> TYPE: PRT
<213> ORGANISM: Vibrio plasmid p0908

<400> SEQUENCE: 10

Met Ile Glu Asn Gln Leu Ser Leu Leu Gly Asp Phe Ser Gly Val Arg
1               5                   10                  15

Pro Asp Asp Val Lys Thr Ala Ile Gln Ala Ala Gln Lys Lys Gly Ile
            20                  25                  30

Asn Val Ala Glu Asn Glu Gln Phe Lys Ala Ala Phe Glu His Leu Leu
        35                  40                  45

Asn Glu Phe Lys Lys Arg Glu Arg Tyr Ser Pro Asn Thr Leu Arg
    50                  55                  60

Arg Leu Glu Ser Ala Trp Thr Cys Phe Val Asp Trp Cys Leu Ala Asn
65                  70                  75                  80

His Arg His Ser Leu Pro Ala Thr Pro Asp Thr Val Glu Ala Phe Phe
                85                  90                  95

Ile Glu Arg Ala Glu Glu Leu His Arg Asn Thr Leu Ser Val Tyr Arg
            100                 105                 110

Trp Ala Ile Ser Arg Val His Arg Val Ala Gly Cys Pro Asp Pro Cys
        115                 120                 125

Leu Asp Ile Tyr Val Glu Asp Arg Leu Lys Ala Ile Ala Arg Lys Lys
    130                 135                 140
```

Val Arg Glu Gly Glu Ala Val Lys Gln Ala Ser Pro Phe Asn Glu Gln
145                 150                 155                 160

His Leu Leu Lys Leu Thr Ser Leu Trp Tyr Arg Ser Asp Lys Leu Leu
            165                 170                 175

Leu Arg Arg Asn Leu Ala Leu Leu Ala Val Ala Tyr Glu Ser Met Leu
            180                 185                 190

Arg Ala Ser Glu Leu Ala Asn Ile Arg Val Ser Asp Met Glu Leu Ala
            195                 200                 205

Gly Asp Gly Thr Ala Ile Leu Thr Ile Pro Ile Thr Lys Thr Asn His
210                 215                 220

Ser Gly Glu Pro Asp Thr Cys Ile Leu Ser Gln Asp Val Val Ser Leu
225                 230                 235                 240

Leu Met Asp Tyr Thr Glu Ala Gly Lys Leu Asp Met Ser Ser Asp Gly
            245                 250                 255

Phe Leu Phe Val Gly Val Ser Lys His Asn Thr Cys Ile Lys Pro Lys
            260                 265                 270

Lys Asp Lys Gln Thr Gly Glu Val Leu His Lys Pro Ile Thr Thr Lys
            275                 280                 285

Thr Val Glu Gly Val Phe Tyr Ser Ala Trp Glu Thr Leu Asp Leu Gly
            290                 295                 300

Arg Gln Gly Val Lys Pro Phe Thr Ala His Ser Ala Arg Val Gly Ala
305                 310                 315                 320

Ala Gln Asp Leu Leu Lys Lys Gly Tyr Asn Thr Leu Gln Ile Gln Gln
            325                 330                 335

Ser Gly Arg Trp Ser Ser Gly Ala Met Val Ala Arg Tyr Gly Arg Ala
            340                 345                 350

Ile Leu Ala Arg Asp Gly Ala Met Ala His Ser Arg Val Lys Thr Arg
            355                 360                 365

Ser Ala Pro Met Gln Trp Gly Lys Asp Glu Lys Asp
            370                 375                 380

<210> SEQ ID NO 11
<211> LENGTH: 34
<212> TYPE: DNA
<213> ORGANISM: Vibrio plasmid p0908

<400> SEQUENCE: 11
tcaatttccg agaatgacag ttctcagaaa ttga                            34

<210> SEQ ID NO 12
<211> LENGTH: 34
<212> TYPE: DNA
<213> ORGANISM: Homo sapiens

<400> SEQUENCE: 12
cagagctctg agactttgtg ttctcaaaga tatc                            34

<210> SEQ ID NO 13
<211> LENGTH: 34
<212> TYPE: DNA
<213> ORGANISM: Homo sapiens

<400> SEQUENCE: 13
aagaggtgtg agactgaatt ttctcagtca ggtt                            34

<210> SEQ ID NO 14
<211> LENGTH: 34

```
<212> TYPE: DNA
<213> ORGANISM: Homo sapiens

<400> SEQUENCE: 14
aagagaactg agaaaatatt ctctcagagg gaat                              34

<210> SEQ ID NO 15
<211> LENGTH: 34
<212> TYPE: DNA
<213> ORGANISM: Mus musculus

<400> SEQUENCE: 15
aacagctttg agagctgttg ctctcagctg aatt                              34

<210> SEQ ID NO 16
<211> LENGTH: 34
<212> TYPE: DNA
<213> ORGANISM: Homo sapiens

<400> SEQUENCE: 16
aacaggactg agataaaaca gtctcagaca gcat                              34

<210> SEQ ID NO 17
<211> LENGTH: 34
<212> TYPE: DNA
<213> ORGANISM: Homo sapiens

<400> SEQUENCE: 17
acaaccattt ataatatata atatgatg ttat                                34

<210> SEQ ID NO 18
<211> LENGTH: 34
<212> TYPE: DNA
<213> ORGANISM: Mus musculus

<400> SEQUENCE: 18
gtaactgagt atatgcatat atacgtat atat                                34

<210> SEQ ID NO 19
<211> LENGTH: 366
<212> TYPE: PRT
<213> ORGANISM: Vibrio tubiashii ATCC 19109

<400> SEQUENCE: 19
```

Met Thr Thr Leu Ser Val Leu Ser Glu Val Pro Phe Glu Arg Leu Leu
1               5                   10                  15

Pro His Glu Phe Ala Glu Gly Leu Ala Ala Gln Arg Ala Gly Glu
            20                  25                  30

Ala Leu Glu Gly His Pro Leu Val Glu Ala Ala Ile Thr His Tyr Gln
        35                  40                  45

Gly Glu Phe Phe Arg Arg Ala Glu Arg Leu Gln Pro Ala Ser Leu Val
    50                  55                  60

Arg Leu Lys Ser Ala Trp Ala Thr Phe Val Ala Trp Cys Cys Glu Gln
65                  70                  75                  80

Asp Arg Cys Ala Leu Pro Ala Ser Pro Gln Thr Val Glu Ala Tyr Leu
                85                  90                  95

Ile Ala Glu Gln Asp Arg Leu His Arg Asn Thr Leu Lys Val Gln Leu
            100                 105                 110

Trp Ala Ile Gly Lys Thr His Gln Ile Ser Gly Cys Pro Asp Pro Cys
        115                 120                 125

```
His Asn Asp Tyr Val Lys Ala Gln Leu Gln Gln Ile His His Arg Lys
    130                 135                 140

Val Arg Gln Arg Glu Val Ile Arg Gln Ala Val Ala Leu Arg Glu Ser
145                 150                 155                 160

His Leu Asn Ala Leu Ala Asp Leu Trp Asp Arg Pro Glu Ala Ser Leu
                165                 170                 175

Thr Glu Cys Arg Asp Leu Leu Ile Val Ser Met Leu Tyr Glu Thr Leu
            180                 185                 190

Leu Arg Lys Ser Asn Leu Glu Thr Leu Arg Val Gly Asp Val Asp Trp
        195                 200                 205

Gln Ala Asp Gly Ser Gly Leu Ile Lys Val Phe Val Thr Lys Thr Asp
    210                 215                 220

Lys Ser Gly Asp Val Lys Tyr Ser Tyr Val Ser Pro Ser Thr Met Asp
225                 230                 235                 240

Leu Leu Ala Arg Tyr Leu Gly His Ala Asp Ile Val Asp Asn Pro Glu
                245                 250                 255

Ala Phe Leu Ile Gln Arg Val Lys Leu Ser Ser Gln Gln Leu Lys Gly
            260                 265                 270

Ser Ala Arg Thr Gln Ala Ala Ile Ser Pro Val Ser Ala Lys Leu Ile
        275                 280                 285

Gly Arg Val Cys Ala Lys Ala Lys Thr Leu Gly Leu Ser Thr Asp
    290                 295                 300

Arg Pro Phe Thr Gly His Ser Ala Arg Val Gly Ala Thr Gln Asp Leu
305                 310                 315                 320

Leu Ala Glu Gly Phe Ser Ser Leu Gln Val Gln Ala Gly Gly Trp
                325                 330                 335

Ser Ser Glu Arg Met Val Leu Arg Tyr Gly Gly Ser Val Leu Ala Ser
            340                 345                 350

Glu Ser Ala Met Ala Gln Arg Gln Arg Lys Ser Pro Lys
        355                 360                 365

<210> SEQ ID NO 20
<211> LENGTH: 34
<212> TYPE: DNA
<213> ORGANISM: Vibrio tubiashii ATCC 19109

<400> SEQUENCE: 20
catacgtcct agaatggcag ttctaggacg tatt                                34

<210> SEQ ID NO 21
<211> LENGTH: 353
<212> TYPE: PRT
<213> ORGANISM: Methylobacterium extorquens DM4

<400> SEQUENCE: 21

Met Glu Leu Val Ala Thr Asp Ser Ala Ala Glu Pro Gln Arg Asp Ala
1               5                   10                  15

Phe Asn Pro Pro Val Pro Phe Ala Asp Ala Leu Pro Pro Gly Leu Glu
                20                  25                  30

Leu Leu Ile Glu Arg Leu Glu Gln His Ala Arg Ala Ala Arg Gly Ala
            35                  40                  45

Phe Ala Asp Asn Thr Val Arg Ala Leu Ala Ala Asp Ser Arg Ile Phe
        50                  55                  60

Ala Ala Trp Cys Arg Glu Glu Gly Arg Ala Met Leu Pro Ala Thr Pro
65                  70                  75                  80

Glu Thr Val Ala Ala Phe Ile Asp Ala Gln Gly Glu Thr Lys Ala Arg
```

```
            85                  90                  95
Ala Thr Val Glu Arg Tyr Arg Ser Ser Ile Ala Ala Leu His Arg Ala
            100                 105                 110

Ala Gly Leu Pro Asn Pro Cys Ala Asp Glu Ile Val Arg Leu Ala Val
        115                 120                 125

Lys Arg Met Asn Arg Ala Arg Gly Arg Arg Gln Lys Gln Ala Glu Pro
130                 135                 140

Leu Asn Arg Ala Ser Ile Glu Arg Met Leu Glu Val Lys Thr Pro Gly
145                 150                 155                 160

Arg Leu His Arg Arg Val Thr Glu Ala Lys Arg Glu Thr Pro Leu Ile
                165                 170                 175

Ala Leu Arg Asn Ala Ala Leu Val Ala Val Ala Tyr Asp Thr Leu Leu
            180                 185                 190

Arg Arg Ser Glu Leu Val Ser Leu Tyr Ile Gly Asp Leu His Lys Gly
        195                 200                 205

Ala Asp Gly Ser Gly Thr Val Leu Val Arg Arg Ser Lys Ala Asp Gln
    210                 215                 220

Glu Gly Glu Gly Ala Ile Lys Tyr Leu Ala Pro Asp Thr Met Ala His
225                 230                 235                 240

Ile Glu Ala Trp Leu Ser Ala Ala His Leu Glu Ser Gly Pro Leu Phe
                245                 250                 255

Arg Pro Leu Thr Lys Gly Gly Gln Val Gly Thr Val Ala Leu Gly Gly
            260                 265                 270

Gly Glu Val Ala Arg Val Phe Arg Asp Leu Ala Thr Ala Ala Gly Leu
        275                 280                 285

Lys Leu Ala Arg Leu Pro Ser Gly His Ser Thr Arg Val Gly Ala Thr
    290                 295                 300

Gln Asp Met Phe Ala Ala Gly Phe Glu Leu Leu Glu Val Met Gln Ala
305                 310                 315                 320

Gly Ser Trp Lys Thr Pro Ala Met Pro Ala Arg Tyr Gly Glu Arg Leu
                325                 330                 335

Arg Ala Gln Arg Gly Ala Ala Arg Lys Leu Ala Thr Leu Gln Asn Arg
            340                 345                 350

Ala

<210> SEQ ID NO 22
<211> LENGTH: 34
<212> TYPE: DNA
<213> ORGANISM: Methylobacterium extorquens DM4

<400> SEQUENCE: 22
atttcccgcg atagatggtg ttatcgcagg caat                               34

<210> SEQ ID NO 23
<211> LENGTH: 386
<212> TYPE: PRT
<213> ORGANISM: Streptomyces sp. W9

<400> SEQUENCE: 23

Met Thr Glu His Asp Gln Gly Glu Val Val Asp Ala Glu Leu Val Asp
1               5                   10                  15

Asp Gln Leu Pro Ala Leu Arg Asn Gln Ala Gln Ala Pro Ala Val Pro
            20                  25                  30

Ala Pro Lys Asn Asp Pro Asp Ala Trp Leu Ser Asp Gln Ala Arg Glu
        35                  40                  45
```

```
Asp Val Lys Ala Gly Ile Ala Asp Gly Thr Arg Asp Gly Tyr Lys Gly
    50                  55                  60
Asp Met Glu Arg Phe Ala Ala Trp Cys Thr Ser Ala Gly Arg Arg Pro
65                  70                  75                  80
Met Pro Ala Ala Pro Gln Thr Val Thr Glu Tyr Leu Ser Tyr Leu Lys
                85                  90                  95
His Thr Pro Arg Pro Arg Thr Asn Lys Pro Tyr Gly Pro Asn Ser Met
            100                 105                 110
Asp Arg Ile Ile Ala Ala Ile Ser Ala His Arg Ala Ala Gly His
            115                 120                 125
Glu Pro Pro Asp Thr Met Gly Ala Arg Lys Val Val Leu Gly Tyr Arg
130                 135                 140
Ala Glu Leu Ser Glu Arg Lys Asp Pro Ala Ala Lys Pro Arg Lys Ala
145                 150                 155                 160
Thr Pro Ala Asp Arg Ala Val Leu Arg Arg Ala Leu Ala Glu Leu Asp
                165                 170                 175
Arg Ala Thr Leu Ala Gly Gln Arg Asp Ala Ala Leu Met Leu Leu Gly
            180                 185                 190
His Ala Leu Ala Ser Arg Gly Ser Glu Leu Val Pro Leu Asn Ile Pro
            195                 200                 205
Asp Ser Phe Thr Asp Leu Pro Asp Gly Gly Phe Ser Val Ala Val Tyr
    210                 215                 220
Arg Lys Lys Arg Lys Cys Trp Gln Asp Val Thr Val Leu Asp Pro
225                 230                 235                 240
Asp Pro Asp Leu Cys Ala Val Arg Ala Val Arg Arg Leu Val Ala Thr
                245                 250                 255
Leu Ala Asp Asn Gly His His Thr Gly Pro Leu Phe Leu Arg Met Asp
            260                 265                 270
Arg Trp Gly Tyr Leu Ala Pro Pro Met His Arg Asn Gly Lys Pro Ile
            275                 280                 285
Gly Asp Pro Thr Gly Arg Met Thr Val Glu Ala Ala Ser Asp Ile Val
    290                 295                 300
Gln Arg Ser Ile Glu Arg Thr Gly Ile Pro Gly Arg Trp Arg Ser His
305                 310                 315                 320
Ser Ser Arg Arg Gly Phe Val Lys Ser Ala Arg Gln Ala Gly Val Asp
                325                 330                 335
Ile Val Gln Ile Gly Arg His Gly Gly Trp Asp Lys Ser Lys Ala
            340                 345                 350
Leu Ile Gly Tyr Ile Asp Glu Glu Asp Ala Gln Gly Asp Asn Asn Pro
            355                 360                 365
Leu Val Gln Ile Gly Arg Lys Ala Ala Leu Pro Pro Asp Ala Ala Ser
    370                 375                 380
Gly Thr
385
```

<210> SEQ ID NO 24
<211> LENGTH: 34
<212> TYPE: DNA
<213> ORGANISM: Streptomyces sp. W9

<400> SEQUENCE: 24 gttgccccg tcgcgcggtc gcgttggggg caac                             34

<210> SEQ ID NO 25
<211> LENGTH: 360

<212> TYPE: PRT
<213> ORGANISM: Streptomyces sp. SPB74

<400> SEQUENCE: 25

Met Ala Ile Arg Arg Gly Ala Leu Thr Ser Gly Pro Asp Arg Ala Lys
1               5                   10                  15

Leu Ser Ala Gly Ala Val Ala Ala Met Glu Lys Gly Ile Pro Pro Glu
            20                  25                  30

Thr Arg Arg Gly Tyr Ala Gly Asp Trp Gln Arg Phe Glu Ala Trp Ala
        35                  40                  45

Phe Gly Glu Gly Ala Cys Pro Leu Pro Cys Ser Ala Glu Thr Leu Thr
    50                  55                  60

Glu Tyr Val Thr Phe Leu Thr Val Phe Pro Arg Pro Arg Thr Gly Met
65                  70                  75                  80

Pro Tyr Glu Pro Ala Pro Ile Glu Arg Ala Met Ala Ala Ile Ala Val
                85                  90                  95

Ala His Lys Ala Ala Gly Phe Ala Pro Pro Asp Thr Thr Gly Ala Arg
            100                 105                 110

Leu Val Leu Arg Gly Tyr Glu Arg Glu Leu Lys Glu Thr Lys Asp Pro
        115                 120                 125

Arg Gly Arg Val Ala Lys Ala Ala Ala Thr Pro Leu Ile Leu Arg
    130                 135                 140

Thr Met Ile Ala His Thr Asp Leu Thr Thr Pro Ile Gly Leu Arg Asp
145                 150                 155                 160

Ala Ala Ala Met Thr Asn Gly Phe Ala Leu Ala Ala Arg Ser Ser Glu
                165                 170                 175

Ala Lys Leu Leu Asp Trp Glu Asp Thr Ala Asp Val Glu Gln Gly Leu
            180                 185                 190

Glu Tyr Asp Leu Tyr Arg Pro Lys Val Asn Asn Asp Gln Pro Leu Gly
        195                 200                 205

Val Pro Tyr Gly Ala Tyr Pro Ser Thr Cys Pro Val Arg Arg Leu His
    210                 215                 220

Ala Trp Arg Gln Cys Leu Leu Asp Leu Gly Tyr Pro Val Ser Gly Pro
225                 230                 235                 240

Ile Tyr Val Arg Ile Asn Arg His Gly His Ile Asn Pro Pro Met Thr
                245                 250                 255

Arg Arg Gly Leu Pro Ile Gly Asp Pro Ser Gly Arg Met Thr Thr Glu
            260                 265                 270

Gly Ile Ala Glu Ile Val Thr Arg Ala Ala Lys Arg Ala Gly Leu Thr
        275                 280                 285

Ala Val Pro Asp Asp Leu Leu Pro Ser Leu Pro Pro Arg Trp Ser Gly
    290                 295                 300

His Ser Leu Arg Arg Gly Tyr Ala Lys Ala Ala Arg Glu Ala Gly Lys
305                 310                 315                 320

Asp Met Leu Glu Ser Gly Arg His Gly Gly Trp Ala Asp Gly Ser Arg
                325                 330                 335

Ala Phe Ala Gly Tyr Phe Asp Arg Ala Ala Ile Trp Asp Glu Asp Leu
            340                 345                 350

Asn Pro Leu Phe Gly Ile Gly Leu
        355                 360

<210> SEQ ID NO 26
<211> LENGTH: 34
<212> TYPE: DNA
<213> ORGANISM: Streptomyces sp. SPB74

-continued

<400> SEQUENCE: 26
ctggctcttg gtaaggcacg ttatcaagag ccaa                                34

<210> SEQ ID NO 27
<211> LENGTH: 346
<212> TYPE: PRT
<213> ORGANISM: Agrobacterium tumefaciens str. C58 plasmid At

<400> SEQUENCE: 27

```
Leu Thr Asp Gln Asp Val Glu Thr Leu Arg His Leu Val Asn Gln Gly
1               5                   10                  15

Met Gly Asp Asn Thr Leu Arg Ala Leu Thr Ser Asp Leu Ala Tyr Leu
            20                  25                  30

Glu Ala Trp Gly Leu Ala Thr Thr Gly Ser Ser Leu Pro Trp Pro Ala
        35                  40                  45

Pro Glu Ala Leu Leu Leu Lys Phe Val Ala His His Leu Trp Asp Pro
    50                  55                  60

Glu Lys Arg Ala Thr Asp Pro Asp His Gly Met Pro Ala Ala Val Asp
65                  70                  75                  80

Glu Asn Leu Arg Arg Gln Gly Phe Leu Arg Ser Val Gly Pro His Ala
                85                  90                  95

Pro Ser Thr Val Arg Arg Leu Ala Asn Trp Ser Thr Leu Thr Arg
            100                 105                 110

Trp Arg Gly Leu His Gly Ala Phe Ala Ser Pro Ala Leu Lys Ser Ala
        115                 120                 125

Ile Arg Leu Ala Val Arg Ala Val Pro Arg Thr Arg Ala Arg Lys Ser
    130                 135                 140

Ala Lys Ala Val Thr Gly Asp Val Leu Ala Lys Leu Leu Ala Thr Cys
145                 150                 155                 160

Glu Ser Asp Ser Leu Arg Asp Leu Arg Asp Lys Ala Ile Leu Met Val
                165                 170                 175

Ala Phe Ala Ser Gly Gly Arg Arg Ser Glu Ile Ala Gly Leu Arg
            180                 185                 190

Arg Glu Gln Leu Thr Ile Glu Ala Pro Ile Glu Thr Glu Gly Gly Pro
        195                 200                 205

Pro Leu Pro Ser Leu Ala Ile His Leu Gly Arg Thr Lys Thr Thr Ser
    210                 215                 220

Gly Glu Glu Asp Asp Thr Val Phe Leu Thr Gly Arg Pro Val Glu Ala
225                 230                 235                 240

Leu Asn Ala Trp Leu Ala Ala Lys Ile Asp Lys Gly Ser Val Phe
                245                 250                 255

Arg Gly Ile Gly Arg Trp Gly Thr Val Ser Arg Ala Leu Asp Pro
            260                 265                 270

Gln Ser Val Asn Ala Ile Leu Lys Gln Arg Ala Glu Met Ala Gly Leu
        275                 280                 285

Glu Ala Gly Gln Phe Ser Ala His Gly Leu Arg Ser Gly Tyr Leu Thr
    290                 295                 300

Glu Ala Ala Asn Arg Gly Ile Pro Leu Pro Glu Ala Met Glu Gln Ser
305                 310                 315                 320

Arg His Arg Ser Val Gln Gln Ala Ser Ser Tyr Tyr Asn Ser Ala Thr
                325                 330                 335

Arg Arg Ser Gly Arg Ala Ala Arg Leu Leu
            340                 345
```

-continued

<210> SEQ ID NO 28
<211> LENGTH: 34
<212> TYPE: DNA
<213> ORGANISM: Agrobacterium tumefaciens str. C58 plasmid At

<400> SEQUENCE: 28
agccatcaag atggcagacg ccatcttgat ggct                             34

<210> SEQ ID NO 29
<211> LENGTH: 405
<212> TYPE: PRT
<213> ORGANISM: Chelativorans sp_ BNC1 plasmid 3

<400> SEQUENCE: 29

Thr Arg Ile Ala Ala Phe Asp Gly Arg Ser Ala Glu Phe Val Ala Pro
1               5                   10                  15

Arg Leu Arg Leu Pro Asn His Ala Arg Ile Ser Thr Met Thr Asn Thr
            20                  25                  30

Val His Gln Pro Ala Asp Asp Leu Pro Asp Ile Val Asp Leu Val Lys
        35                  40                  45

Glu Met Cys Arg Pro Thr Gln Leu Glu Arg Gln Ser Gly Ser Asp Lys
    50                  55                  60

Pro Asn Pro Pro Ala Leu Pro Ala Ala His Arg Ala Glu Asn Gln Ile
65                  70                  75                  80

Pro Ser His Leu Asp Gly Leu Ala Asp Arg Ala Arg Gly Tyr Val Glu
                85                  90                  95

Ala Ala Ser Ser Ser Asn Thr Arg Arg Ala Tyr Ala Ser Asp Trp Lys
            100                 105                 110

His Phe Ala Ser Trp Cys Arg Arg Gln Gly Phe Ser Leu Met Pro Pro
        115                 120                 125

Asp Pro Gln Thr Val Gly Leu Tyr Ile Thr Ala Gln Ala Ser Ala Ser
    130                 135                 140

Gly Arg Asp Lys Lys Ser Val Ser Thr Ile Glu Arg Arg Leu Ser Ser
145                 150                 155                 160

Leu Thr Trp Asn Tyr Ser Gln Arg Gly Gln Pro Leu Asp Arg Lys Asp
                165                 170                 175

Arg His Ile Ala Thr Val Met Ala Gly Ile Arg Asn Lys His Ala Ser
            180                 185                 190

Pro Pro Arg Gln Lys Glu Ala Ile Leu Arg Asp Leu Val Ala Met
        195                 200                 205

Leu Glu Thr Leu Asp Arg Gly Ser Leu Arg Gly Leu Arg Asp Arg Ala
    210                 215                 220

Met Leu Leu Leu Gly Phe Ala Gly Gly Leu Arg Arg Ser Glu Ile Val
225                 230                 235                 240

Gly Leu Asp Val Ala Arg Asp Gln Thr Glu Asp Gly Arg Gly Trp Ile
                245                 250                 255

Glu Ile Leu Asp Lys Gly Met Leu Val Ser Leu Arg Gly Lys Thr Gly
            260                 265                 270

Trp Arg Glu Val Glu Ile Gly Arg Gly Ser Ser Asp Ala Thr Cys Pro
        275                 280                 285

Ile Val Ala Leu Glu Thr Trp Met Lys Phe Ala Arg Ile Ala His Gly
    290                 295                 300

Pro Val Phe Arg Arg Val Thr Gly Gln Ser Lys Ala Val Gly Ala Asp
305                 310                 315                 320

Arg Leu Lys Asp Gln Glu Val Ala Arg Leu Val Lys Arg Ala Ala Leu

```
            325                 330                 335
Ala Ala Gly Val Arg Gly Asp Leu Pro Glu Gly Glu Arg Gly Gln Lys
        340                 345                 350

Phe Ala Gly His Ser Leu Arg Ala Gly Leu Ala Ser Ser Ala Glu Val
        355                 360                 365

Asp Glu Arg Tyr Val Gln Lys Gln Leu Gly His Ala Ser Ala Glu Met
        370                 375                 380

Thr Arg Lys Tyr Gln Arg Arg Asp Arg Phe Arg Val Asn Leu Thr
385                 390                 395                 400

Lys Ala Ser Gly Leu
                405

<210> SEQ ID NO 30
<211> LENGTH: 34
<212> TYPE: DNA
<213> ORGANISM: Chelativorans sp_ BNC1 plasmid 3

<400> SEQUENCE: 30
acatcgagcg gctccgcgac gaaccgcgcg atgt                                34

<210> SEQ ID NO 31
<211> LENGTH: 347
<212> TYPE: PRT
<213> ORGANISM: Marinobacter aquaeolei VT8 plasmid pMAQU02

<400> SEQUENCE: 31

Met Asn Glu Asn Ser His Lys Lys Pro Pro Asp Leu Thr Leu Arg Asn
1               5                   10                  15

Glu Gly Ser Ala Val Ser Ile His Met Glu Ser Glu Ala Leu Arg His
                20                  25                  30

Tyr Leu Gln Ala Ala Thr Thr Asp Asn Thr Arg Lys Ala Tyr Arg Ser
            35                  40                  45

Ala Ile Arg Gln Phe Glu Lys Trp Gly Gly Arg Leu Pro Thr Asp Arg
        50                  55                  60

Asp Thr Val Val Arg Tyr Leu Leu Ser Lys Ala Lys Ser Leu Asn Ser
65                  70                  75                  80

Arg Thr Leu Asn Leu His Leu Thr Ala Ile Gly Gln Trp His His Tyr
                85                  90                  95

Gln Gly Ile Thr Asp Pro Val Arg Asp Pro Leu Val Arg Lys Thr Met
                100                 105                 110

Asp Gly Ile Arg Arg Thr His Gly Gln Pro Lys Arg Lys Ala Lys Ala
            115                 120                 125

Leu Arg Leu Glu His Ile Ala Gln Met Val Lys His Leu Gln Arg Leu
        130                 135                 140

Pro Asp Cys Asn Lys Lys Tyr Arg Asp Ile Ala Met Val Leu Thr Gly
145                 150                 155                 160

Phe Phe Gly Ala Phe Arg Arg Ser Glu Leu Val Ala Ile Arg Val Ser
                165                 170                 175

Asp Leu Ile Trp Glu Pro Glu Gly Leu Ile Ile Lys Met Pro Arg Ser
            180                 185                 190

Lys Thr Asp Gln Glu Ala Glu Gly Leu Met Arg Ala Leu Pro Phe Gly
        195                 200                 205

Asp Val Ala Val Cys Pro Val Gln Ala Leu Lys Ser Trp Leu Glu Glu
    210                 215                 220

Ala Glu Ile Arg Glu Gly Pro Val Phe Arg Pro Val Asn Arg Trp Asp
225                 230                 235                 240
```

```
Gln Ile Gln Pro Arg Pro Leu Thr Pro Ser Ser Ile Asn Asp Leu Leu
                245                 250                 255

Lys Ala Leu Gly Lys Ala Cys Asp Phe Asp Phe Ile His Glu Leu Ser
            260                 265                 270

Ser His Ser Phe Arg Arg Gly Leu Ser Thr Ser Ala Ala Arg Glu Arg
        275                 280                 285

Ile Asp Phe Glu Leu Ile Lys Lys Gln Gly Gly Trp Arg Ser Asp Ala
    290                 295                 300

Thr Val Trp Ala Tyr Val Glu Glu Gly Gln Gln Leu Ser Glu Asn Ala
305                 310                 315                 320

Ala Val Val Leu Met Glu Lys Leu Gln Ala Leu Met Lys Pro Glu Pro
                325                 330                 335

Asn Gln Glu His Ser Thr Gly Ala Ile Ile Glu
            340                 345

<210> SEQ ID NO 32
<211> LENGTH: 34
<212> TYPE: DNA
<213> ORGANISM: Marinobacter aquaeolei VT8 plasmid pMAQU02

<400> SEQUENCE: 32
ctaacccacg ataatcaatc ttatcgcggg ttaa                            34

<210> SEQ ID NO 33
<211> LENGTH: 351
<212> TYPE: PRT
<213> ORGANISM: Pseudomonas sp. ND6 plasmid pND6-1

<400> SEQUENCE: 33

Val Ser Ile Ile Cys Gly Thr His Gly Leu Asn Arg Arg Phe Val Met
1               5                   10                  15

Thr Ala Gly Asn Asn Asp Glu Asn Leu Pro Thr Arg Arg His Glu Glu
            20                  25                  30

Pro Thr Val Leu Ala Arg Thr Pro Gly Thr Leu Thr Thr Pro Glu Gln
        35                  40                  45

Leu Ala Glu Gln His Gln Arg Phe Leu Ala Ala Thr Thr Asp Asn
    50                  55                  60

Thr Arg Arg Thr Tyr Arg Ser Ala Ile Arg His Phe Leu Ala Trp Gly
65                  70                  75                  80

Gly Val Leu Pro Cys Asp Glu Ala Leu Ile Arg Tyr Leu Leu Ser
                85                  90                  95

Phe Ala Glu Val Leu Asn Pro Arg Thr Leu Ala Leu Arg Leu Thr Ala
                100                 105                 110

Leu Ser Gln Trp His Arg Tyr Gln Gly Phe Pro Asp Pro Thr Ala Ser
            115                 120                 125

Ala Thr Val Gly Lys Thr Leu Arg Gly Ile Glu Arg Val Asn Gly Arg
    130                 135                 140

Pro Arg Gln Lys Ala Lys Ala Leu Val Leu Glu Asp Leu Glu Arg Ile
145                 150                 155                 160

Val Val His Leu Asn Thr Leu Asp Gly Leu Ala Thr Leu Arg Asp Ser
                165                 170                 175

Ala Leu Leu Gln Val Gly Tyr Phe Gly Ala Phe Arg Arg Ser Glu Leu
            180                 185                 190

Val Thr Leu Glu Met Gln Tyr Leu Glu Trp Glu Gln Glu Gly Leu Arg
        195                 200                 205
```

```
Ile Thr Leu Pro Arg Ser Lys Thr Asp Gln Glu Gly Glu Gly Leu Asp
    210                 215                 220

Lys Ala Ile Pro Tyr Gly Asp Ser Ile Cys Cys Pro Ala Thr Ala Leu
225                 230                 235                 240

Arg Arg Trp Leu Asp Ala Ala Gln Ile Val Gln Gly Pro Leu Phe Arg
                245                 250                 255

Arg Ile Ser Arg Trp Gly Val Leu Gly Glu Val Ala Leu His Glu Gly
            260                 265                 270

Ser Val Asn Thr Ile Leu Thr Ala Arg Ala Glu Ala Ala Gly Leu Leu
        275                 280                 285

Tyr Val Pro Glu Leu Ser Ser His Ser Leu Arg Arg Gly Leu Ala Thr
    290                 295                 300

Ser Ala His Arg Ala Gly Ala Asp Phe Leu Glu Ile Lys Arg Gln Gly
305                 310                 315                 320

Gly Trp Arg His Asp Gly Thr Val His Gly Tyr Ile Glu Glu Ala Gly
                325                 330                 335

Ala Phe Glu Glu Asn Ala Ala Gly Ser Leu Leu Arg Arg Lys Pro
            340                 345                 350

<210> SEQ ID NO 34
<211> LENGTH: 34
<212> TYPE: DNA
<213> ORGANISM: Pseudomonas sp. ND6 plasmid pND6-1

<400> SEQUENCE: 34
ttgacccacg ataagcgcgg ttatcgtgag ttaa                              34

<210> SEQ ID NO 35
<211> LENGTH: 343
<212> TYPE: PRT
<213> ORGANISM: Pantoea sp. aB

<400> SEQUENCE: 35

Met Lys His Leu Ala Gln Ile Lys Thr Gly Ala Leu Pro Ala Glu Leu
1               5                   10                  15

Thr Gln Leu Thr Pro Glu Asp Ile Ala Asn Asn Leu Arg Arg Phe Ile
            20                  25                  30

Ala Asp Lys Ala Ala Tyr Ser Glu Asn Thr Phe Arg Asp Leu Leu Ser
        35                  40                  45

Val Ile Arg Arg Trp Ala Phe Trp Cys Asn Glu Arg Asp Val Gly Tyr
    50                  55                  60

Leu Pro Ile Asp Pro Glu Leu Ala Arg Glu Tyr Phe Leu Gln Met Ala
65                  70                  75                  80

Glu Ser Gly Leu Ala Ser Ser Thr Ile Asp Lys His Tyr Ala Met Met
                85                  90                  95

Asn Met Leu Cys Arg Glu Ser Gly Leu Pro Asp Leu Arg Gly Ser Val
            100                 105                 110

Asp Leu Lys Arg Ser Met Lys Arg Ile Arg Arg Glu Ala Val Leu Gln
        115                 120                 125

Gly Glu Arg Thr Gly Gln Ala Val Pro Phe Arg Leu Pro Asp Leu Gln
130                 135                 140

Leu Leu Ser His Leu Met Gly Arg Ser Asp Arg Leu Thr Asp Gln Arg
145                 150                 155                 160

Asn Leu Ala Phe Leu Phe Val Ala Tyr Asn Thr Leu Cys Arg Met Ser
                165                 170                 175

Glu Leu Ser Arg Ile Arg Val Arg Asp Leu Asp Ile Ser Asp Ser Gly
```

```
                180                 185                 190
His Val Ile Asn Leu Ser His Thr Lys Thr Met Val Thr Ala Ala
            195                 200                 205

Gly Val Ile Lys His Leu Ser Arg Ala Ala Gly His Leu Met His
210                 215                 220

Trp Leu Glu Leu Ser Gly Leu Ile His His Pro Asp Ala Met Val Phe
225                 230                 235                 240

Gly Pro Val Arg His Asn Asn Thr Ala Gly Val Ser Glu Lys Pro Met
            245                 250                 255

Ser Ala Pro Ala Thr Glu Lys Ile Phe Lys Asp Ala Trp Asp Leu Leu
            260                 265                 270

Gly Lys Glu Pro Val Gln Asp Asn Lys Gly Arg Tyr Ala Lys Trp Ser
            275                 280                 285

Gly His Ser Ala Arg Val Gly Ala Ala Met Asp Met Ala Glu Arg Asp
            290                 295                 300

Ala Thr Ile Thr Gln Ile Met Gln Glu Gly Thr Trp Gln Asp Pro Lys
305                 310                 315                 320

Thr Val Met Arg Tyr Leu Arg Arg Ser Glu Ser Gln Lys Gly Lys Met
                325                 330                 335

Ser Gly Ile Leu Asp Gly Glu
            340
```

<210> SEQ ID NO 36
<211> LENGTH: 34
<212> TYPE: DNA
<213> ORGANISM: Pantoea sp. aB

<400> SEQUENCE: 36
gaaactttaa ataataagtc ttatataaag tttc                          34

<210> SEQ ID NO 37
<211> LENGTH: 460
<212> TYPE: PRT
<213> ORGANISM: Vibrio nigripulchritudo

<400> SEQUENCE: 37

```
Met Asp Lys His His Leu Leu Ser Thr Arg Thr Thr Ala Pro Thr Asp
1               5                   10                  15

Gly Ser Asp Phe Asn Ser Asp Asn Val Thr Lys Asn His His Ala Ile
            20                  25                  30

Leu Ile Glu Arg Ala Leu Ala Ser Ala Leu Ala Arg Pro Gly Leu Leu
        35                  40                  45

Leu Glu Thr His Phe Gln Pro Ile Tyr Gln Arg Ala Asp Arg Leu Gly
    50                  55                  60

Val Asp Leu Ser Asp Cys Pro Ser Phe Phe Val Ala Thr Gln Arg Leu
65                  70                  75                  80

Leu Ala Gln His His Gln His Gly Ala Gly Leu Ser Pro Arg Ser Leu
                85                  90                  95

Glu Gln Phe His Ser Ala Val Arg Val Phe Thr Gln Trp Cys His Val
            100                 105                 110

Asn Arg Arg Thr Ala Leu Pro Ala Ser Ala Asp Thr Phe Val Leu Phe
        115                 120                 125
```

```
Ala Arg Ser Asn Ala Pro His Ile Thr Leu Ser Thr Leu His Ile Tyr
    130                 135                 140
Val Trp Ala Ile Arg Lys Leu His Leu Ile Thr Gly Leu Val Asp Pro
145                 150                 155                 160
Thr Asp Ser Gln Ala Val Lys Gln His Leu Ser Arg Ile Lys Lys Gln
                165                 170                 175
Lys Ile Ala Gln Phe Asp Thr Ala Gln Asp Gln Ala Val Pro Leu Ser
                180                 185                 190
Asp Glu Asp Tyr Arg Thr Ala Met Thr Leu Leu Met Ala Asp Asp His
            195                 200                 205
Pro Ile Ser Trp Arg Asp Ala Thr Leu Leu Gly Leu Ala Tyr His Thr
    210                 215                 220
Met Leu Arg Gln Ser Glu Leu Val Arg Ile Gln Leu Thr His Ile Gln
225                 230                 235                 240
Pro Arg Ser Asp Gly Asp Trp Thr Leu Glu Ile Pro Tyr Thr Lys Thr
                245                 250                 255
Asn Lys Thr Gly Arg Ser Glu Tyr Val Thr Leu Pro His Tyr Leu Met
                260                 265                 270
Pro Ile Leu Gln Arg Tyr Leu Ser Leu Cys Gly Asp Arg Thr Leu Thr
            275                 280                 285
Asp Pro Gly Tyr Leu Phe Val Pro Leu Thr Arg Ser Gly Val Pro Arg
    290                 295                 300
Arg Gln Arg Met His Val Thr Ser Thr Pro Arg Ala Pro Ser Gly Val
305                 310                 315                 320
Thr Pro Arg Arg Lys Thr Arg Gly Gly Ile Gln Phe Ala Pro Val Ala
                325                 330                 335
Pro Asp Ala Val Thr Asp Ser Ile Ala Ala Pro Pro Asp Pro Ala Pro
            340                 345                 350
Ile Ser Glu Glu Val Gln Pro Val Ala Pro Lys Leu Val Ala Arg Thr
    355                 360                 365
Leu Lys Lys Ile Gly Glu Arg Leu Ala Thr His Thr Ser Ser Pro Gln
370                 375                 380
Ala Asp Arg Ala Tyr Ser Gly His Ser Ala Arg Val Gly Arg Ala Ile
385                 390                 395                 400
His Leu Leu Glu Ile Gly Ala Arg Lys Glu Asp Ile Val Lys Ala Gly
                405                 410                 415
Arg Trp Lys Ser Asp Ile Met Phe Glu Arg Tyr Thr Arg Gln Tyr Asp
            420                 425                 430
Val Asn Asp Gly Tyr Leu Ala Gln Ile Arg Gln Ala Glu Asp Arg His
    435                 440                 445
Trp His Ala Gln Thr Glu Pro Pro Asp Ser Thr Gly
    450                 455                 460
```

<210> SEQ ID NO 38
<211> LENGTH: 34
<212> TYPE: DNA
<213> ORGANISM: Vibrio nigripulchritudo

<400> SEQUENCE: 38
tgaatgtcct ataattacac ttataggaca ttca                       34

PROTEIN WITH RECOMBINASE ACTIVITY FOR SITE-SPECIFIC DNA-RECOMBINATION

REFERENCE TO SEQUENCE LISTING SUBMITTED ELECTRONICALLY

The content of the electronically submitted sequence listing (Name: 2846_0020002_Seqlisting_ST25.txt; Size: 53 kilobytes; and Date of Creation: Sep. 12, 2016) filed with the application is incorporated herein by reference in its entirety.

The invention relates to the use of a protein with recombinase activity to catalyze a site-specific DNA recombination and a method for producing a site-specific DNA recombination. The invention is applicable alone or in combination with other recombinase systems for genetic manipulation, for example in medical research.

The use of site-specific DNA recombinases allows genetic manipulations in both prokaryotic and eukaryotic organisms. For this purpose, various site-specific DNA recombinases isolated from different organisms are used. The DNA recombination mediated by the site-specific recombinase occurs by cleavage and rejoining of DNA at specific DNA sequences, the so-called recognition sites (nucleic acid sequences of 10 to 150 base pairs). If two recognition sites are oriented in the same direction in a DNA strand, a nucleic acid segment flanked by the recognition sites is cut out (excision). If two recognition sequences flanking a nucleic acid segment in a DNA strand are oriented in the opposite direction, the site-specific DNA recombinase catalyzes the inversion of the nucleic acid segment. If two recombination sites are located on two different molecules, then the site-specific DNA recombinase catalyzes merge of two molecules (integration).

Among sites-specific recombinases a particular class called tyrosine recombinases (SSRs), such as Cre and Flp, has become an outstanding genetic tool. Unlike most SSRs, they do not require additional host factors for efficient catalysis and recognize relatively short sequences. Because of the simplicity and efficiency, these recombinases now serve as "molecular scissors" for robust, non-disruptive and reproducible genomic modifications.

The so-called Cre/loxP system (EP 0 2200 009 B1) is widely used in the prior art. Cre (amino acid sequence according to SEQ ID No. 4) is a site-specific DNA recombinase isolated from bacteriophage P1. The recognition site of the Cre protein is a nucleotide sequence of 34 base pairs, the so-called loxP site (SEQ ID No. 5). Cre shows high recombinase activity both in bacterial and mammalian cells. It is known to modify the amino acid sequence of Cre in order to obtain novel site-specific recombinases (DE 102 07 313 A1).

Another site-specific DNA recombinase system is the so-called Flp/FRT system isolated from *Saccharomyces cerevisiae*. The Flp/FRT system includes the recombinase Flp (flippase) (amino acid sequence according to SEQ ID No. 6) that catalyzes DNA-recombination on its recognition sites, the so-called FRT sites (SEQ ID No. 7).

In addition to the Cre/loxP and the Flp/FRT system, that are both the most widely used site-specific recombinase systems of tyrosine class, other recombinase systems are known in the art. U.S. Pat. No. 7,422,889 and U.S. Pat. No. 7,915,037 B2 disclose the so-called Dre/rox system that comprises a Dre recombinase (amino acid sequence according to SEQ ID No. 8) isolated from Enterobacteria phage D6, the recognition site of which is called rox-site (SEQ ID No. 9). Further known recombinase systems are the VCre/VloxP system isolated from *Vibrio* plasmid p0908 (amino acid sequence according to SEQ ID No. 10 for the recombinase, and SEQ ID No. 11 for the VloxP site), and the sCre/SloxP system (WO 2010/143606 A1; Suzuki and Nakayama, 2011).

The known recombinase systems that are known in the art show different activities in cells of different origin. For many applications, such as the production of transgenic animals with conditional gene knockouts, two or more recombinase systems are used in combination with each other. However, emerging complex genetics studies and applications require simultaneous use of multiple recombinases. At the same time not all well-described site-specific recombinases are equally applicable in all model organisms due to, e.g. genome specificity (off-target activity on cryptic recognition target sites). For that reason it is important that an optimal recombinase can be chosen depending on the target organism or experimental setup. Therefore, there is a need for the provision of alternative recombinase systems that can be used to catalyze a site-specific DNA recombination on short targets in a variety of cell types and with high activity and with low toxicity. It is the objective of the invention to provide novel recombinase systems for site-specific genetic recombination that can be used in a variety of cell types. Another object of the invention is to provide a novel, highly specific, recombinase system for site-specific genetic recombination with preferably low toxicity.

The objective is solved by the use of a protein with recombinase activity, wherein the protein comprises an amino acid sequence exhibiting at least 70%, preferably at least 80%, preferably at least 90%, particularly preferred at least 95%, even more preferred at least 99% amino acid sequence identity to SEQ ID No. 1 to catalyze a site-specific DNA recombination at, preferably at two, recognition sites that are identical or reverse complementary to each other, wherein at least one recognition site comprises a nucleic acid sequence according to or reverse complementary to SEQ ID No. 2; or a nucleic acid sequence that is a functional mutant thereof.

The protein with recombinase activity as defined above and used in the invention protein is referred to herein as "Vika". The recognition site of the site-specific recombinase Vika is referred to herein as "vox-site" or simply "vox". A vox-site is characterized by its nucleic acid sequence according to SEQ ID No. 2 or a nucleic acid sequence reverse complementary thereto. Recognition sites that exhibit a nucleic acid sequence identity to SEQ ID No. 2 of at least 70%, preferably at least 80%, preferably at least 90%, particularly preferred at least 95%, even more preferred at least 99%, or nucleic acid sequences reverse complementary thereto; and that are targets for the site specific recombination of Vika (herein referred to as "functional mutants" of vox sites) are also "vox-sites" within the sense of the invention. However, particularly preferred vox-sites exhibit a nucleic acid sequence according to SEQ ID No. 2 or a nucleic acid sequence reverse complementary thereto (herein also referred to as "wild type vox-site").

By a functional mutant of the wild type vox-site is meant that one or more nucleic acids are added to, inserted, deleted or substituted from the nucleic acid sequence according to SEQ ID No. 2. At the same time, the functional mutant of the recognition site with a nucleic acid sequence according to SEQ ID No. 2 exhibits a nucleic acid sequence identity to SEQ ID No. 2 of at least 70%, preferably at least 80%, preferably at least 90%, particularly preferred at least 95%, even more preferred at least 99% and is a functional recognition site of Vika. Preferred mutations are point mutations or an exchange of the spacer region of the recognition site according to SEQ ID No. 2. It is known that the exchange of a spacer region of a recognition site does not influence its activity as a target site for the specific recombinase. Therefore, particularly preferred functional mutants of the wild type vox-site exhibit a nucleic acid sequence identity of at least 70%, preferably at least 75%, to the nucleic acid sequence according to SEQ ID No. 2 or its reverse complementary sequence; and exhibit mutations in the nucleic acids 14 to 21 (spacer region) of SEQ ID No. 2.

The invention is based on the finding of the inventors that the protein ZP_05884863 (www.ncbi.nlm.nih.gov/protein/ZP_05884863, SEQ ID No. 1), which is referred to herein as Vika (wild type), shows a Cre recombinase-like activity and recognizes recognition sites according to SEQ ID No. 2. Vika is derived from the gram-negative bacterium *Vibrio coralliilyticus* ATCC BAA 450. The amino acid sequences of Cre and Vika show a low identity of merely 26% (49% sequence similarity). The recognition sequences for Cre and Vika show a low identity of 35.6% (35.6% sequence similarity).

The inventors identified six putative recognition sites with a lox-like structure in *Vibrio coralliilyticus*. Upon extensive studies only one thereof, the wild type vox site, turned out to be the actual recognition site of Vika. The wild type vox-site is a 34 bp region of two inverted repeats that comprises about 50% sequence homology to the loxP site. By expression of the nucleic acid sequence encoding for Vika (SEQ ID No. 3) in *E. coli*, the Vika protein could be successfully obtained and its recombinase activity and specificity for the wild type vox site could be demonstrated. Vika was shown to belong to tyrosine class of SSRs and therefore, as further demonstrated in experiments, does not require expression of auxiliary factors for enzymatic activity in various cells types. Furthermore, it was shown that Vika does not cross react with other known recombinase systems and is superior in the activity compared to some of the known recombinase systems, at least in certain cell types.

The invention is based further on the finding that the protein WP_008927019.1 (www.ncbi.nlm.nih.gov/protein/WP_008927019.1, SEQ ID No. 35), which is referred to herein as Panto (wild type), shows a Cre recombinase-like activity and recognizes recognition sites according to SEQ ID No. 36. Panto is derived from the enterobacterium *Panteo* sp. aB. The amino acid sequences of Cre and Panto show a low identity of 41% (57% sequence similarity).

The invention is based further on the finding that the protein YP_004250912. (www.ncbi.nlm.nih.gov/protein/YP_004250912.1, SEQ ID No. 37), which is referred to herein as Nigri (wild type), which was already predicted to be a putative Cre-like recombinase, recognizes recognition sites according to SEQ ID No. 38. Nigri is derived from the gram-negative bacterium *Vibrio nigripulchritudo*. The recognition sequences for Cre and Nigri show a low identity of 34.7% (34.7% sequence similarity).

The inventors identified recognition sites for both Panto and Nigri.

The objective is further solved by the use of a protein with recombinase activity, wherein the protein comprises an amino acid sequence exhibiting at least 70%, preferably at least 80%, preferably at least 90%, particularly preferred at least 95%, even more preferred at least 99% amino acid sequence identity to SEQ ID No. 35 to catalyze a site-specific DNA recombination at, preferably at two, recognition sites that are identical or reverse complementary to each other, wherein at least one recognition site comprises a nucleic acid sequence according to or reverse complementary to SEQ ID No. 35; or a nucleic acid sequence that is a functional mutant thereof.

The protein with recombinase activity as defined above and used in the invention protein is referred to herein as "Panto". The recognition site of the site-specific recombinase Panto is referred to herein as "pox-site" or simply "pox". A pox-site is characterized by its nucleic acid sequence according to SEQ ID No. 36 or a nucleic acid sequence reverse complementary thereto. Recognition sites that exhibit a nucleic acid sequence identity to SEQ ID No. 36 of at least 70%, preferably at least 80%, preferably at least 90%, particularly preferred at least 95%, even more preferred at least 99%, or nucleic acid sequences reverse complementary thereto; and that are targets for the site specific recombination of Panto (herein referred to as "functional mutants" of pox sites) are also "pox-sites" within the sense of the invention. However, particularly preferred pox-sites exhibit a nucleic acid sequence according to SEQ ID No. 36 or a nucleic acid sequence reverse complementary thereto (herein also referred to as "wild type pox-site").

By a functional mutant of the wild type pox-site is meant that one or more nucleic acids are added to, inserted, deleted or substituted from the nucleic acid sequence according to SEQ ID No. 36. At the same time, the functional mutant of the recognition site with a nucleic acid sequence according to SEQ ID No. 36 exhibits a nucleic acid sequence identity to SEQ ID No. 36 of at least 70%, preferably at least 80%, preferably at least 90%, particularly preferred at least 95%, even more preferred at least 99% and is a functional recognition site of Panto. Preferred mutations are point mutations or an exchange of the spacer region of the recognition site according to SEQ ID No. 36. It is known that the exchange of a spacer region of a recognition site does not influence its activity as a target site for the specific recombinase. Therefore, particularly preferred functional mutants of the wild type pox-site exhibit a nucleic acid sequence identity of at least 70%, preferably at least 75%, to the nucleic acid sequence according to SEQ ID No. 36 or its reverse complementary sequence.

The objective is further solved by the use of a protein with recombinase activity, wherein the protein comprises an amino acid sequence exhibiting at least 70%, preferably at least 80%, preferably at least 90%, particularly preferred at least 95%, even more preferred at least 99% amino acid sequence identity to SEQ ID No. 37 to catalyze a site-specific DNA recombination at, preferably at two, recognition sites that are identical or reverse complementary to each other, wherein at least one recognition site comprises a nucleic acid sequence according to or reverse complementary to SEQ ID No. 37; or a nucleic acid sequence that is a functional mutant thereof.

The protein with recombinase activity as defined above and used in the invention protein is referred to herein as "Nigri". The recognition site of the site-specific recombinase Nigri is referred to herein as "nox-site" or simply "nox". A nox-site is characterized by its nucleic acid sequence according to SEQ ID No. 38 or a nucleic acid sequence reverse complementary thereto. Recognition sites that exhibit a nucleic acid sequence identity to SEQ ID No. 38 of at least 70%, preferably at least 80%, preferably at least 90%, particularly preferred at least 95%, even more preferred at least 99%, or nucleic acid sequences reverse complementary thereto; and that are targets for the site specific recombination of Nigri (herein referred to as "functional mutants" of nox sites) are also "nox-sites" within the sense of the invention. However, particularly preferred nox-sites exhibit a nucleic acid sequence according to SEQ ID No. 38 or a nucleic acid sequence reverse complementary thereto (herein also referred to as "wild type nox-site").

By a functional mutant of the wild type nox-site is meant that one or more nucleic acids are added to, inserted, deleted or substituted from the nucleic acid sequence according to SEQ ID No. 38. At the same time, the functional mutant of the recognition site with a nucleic acid sequence according to SEQ ID No. 38 exhibits a nucleic acid sequence identity to SEQ ID No. 38 of at least 70%, preferably at least 80%, preferably at least 90%, particularly preferred at least 95%, even more preferred at least 99% and is a functional recognition site of Nigri. Preferred mutations are point mutations or an exchange of the spacer region of the recognition site according to SEQ ID No. 38. It is known that the exchange of a spacer region of a recognition site does not influence its activity as a target site for the specific recombinase. Therefore, particularly preferred functional mutants of the wild type nox-site exhibit a nucleic acid sequence identity of at least 70%, preferably at least 75%, to the nucleic acid sequence according to SEQ ID No. 38 or its reverse complementary sequence.

Within the sense of the invention the terms "site-specific DNA recombinase" and "recognition site" are used as defined above in the discussion of the prior art.

The invention also includes a method for producing a site-specific DNA recombination. The method according to the invention comprises the steps of
a) providing a cell comprising at least two recognition sites that are identical or reverse complementary to each other, wherein at least one recognition site comprises a nucleic acid sequence according to or reverse complementary to SEQ ID No. 2; or a nucleic acid sequence that is a functional mutant thereof; and
b) contacting a protein with recombinase activity, wherein the protein exhibits an amino acid sequence of at least 70%, preferably at least 80%, preferably at least 90%, particularly preferred at least 95%, even more preferred at least 99%, amino acid sequence identity to SEQ ID No. 1 with the recognition sites, thereby producing the site-specific DNA-recombination.

In this method according to the invention the Vika protein is contacted with at least two vox sites preferably inside a cell. Upon binding of the Vika protein to the vox sites, site-specific DNA-recombination occurs.

The invention further includes a method for producing a site-specific DNA recombination using Panto or Nigri. The method according to the invention comprises the steps of
a) providing a cell comprising at least two recognition sites that are identical or reverse complementary to each other, wherein at least one recognition site comprises a nucleic acid sequence according to or reverse complementary to SEQ ID No. 36 or 38; or a nucleic acid sequence that is a functional mutant thereof; and
b) contacting a protein with recombinase activity, wherein the protein exhibits an amino acid sequence of at least 70%, preferably at least 80%, preferably at least 90%, particularly preferred at least 95%, even more preferred at least 99%, amino acid sequence identity to SEQ ID No. 35 or 37 with the recognition sites, thereby producing the site-specific DNA-recombination.

In this method according to the invention the Panto protein is contacted with at least two pox sites inside a cell. Alternatively the Nigri protein is contacted with at least two nox sites inside a cell. Upon binding of the Panto or Nigri protein to the pox sites or respectively to the nox sites, site-specific DNA-recombination occurs.

The method according to the invention can be carried out in vitro or in vivo. In case the invention is carried out in an animal (including humans) it is preferably carried out for non-therapeutic use. The method is applicable in all areas where state of the art site specific recombinases are conventionally used (including inducible knock out or knock in mice and other transgenic animal models). In preferred methods according to the invention, the site-specific recombination results in integration, deletion, inversion, translocation or exchange of DNA. Preferably, the method according to the invention is not used for the therapeutic treatment of a human being or an animal. Preferably the method according to the invention is used to create animal models, which are useful for biomedical research, e. g. as models for human diseases.

In a method according to the invention, the nucleic acid sequence encoding for Vika (or Panto or Nigri respectively) is either already present in the cell or introduced into the cell, preferably by recombinant techniques. This preferred method according to the invention further includes the step of
c) introducing into the cell a nucleic acid encoding for the Vika protein (or the Panto or Nigri protein respectively) with recombinase activity, wherein said nucleic acid encoding for the Vika protein preferably exhibits at least 70%, preferably at least 80%, preferably at least 90%, particularly preferred at least 95%, even more preferred at least 99% nucleic acid sequence identity to SEQ ID No. 3.

For activation of the expression of the nucleic acid encoding for Vika (or Panto or Nigri respectively), the nucleic acid encoding for Vika (or Panto or Nigri respectively) further comprises a regulatory nucleic acid sequence, preferably a promoter region. Hence, expression of the nucleic acid encoding for the protein with recombinase activity is produced by activating the regulatory nucleic acid sequence. Accordingly, to induce a DNA recombination, the regulatory nucleic acid sequence (preferably the promoter region) is activated to express the gene encoding for the Vika protein (or the Panto or Nigri protein respectively). Preferably, the regulatory nucleic acid sequence (preferably the promoter region) is either introduced into the cell in the method of the invention, preferably together with the sequence encoding for Vika (or Panto or Nigri respectively), or the regulatory nucleic acid sequence is already present in the cell in the beginning of the method according to the invention. In the second case, merely the nucleic acid encoding for the Vika (or Panto or Nigri respectively) protein is introduced into the cell (and placed under the control of the regulatory nucleic acid sequence).

By the term "regulatory nucleic acid sequences" within the sense of the invention gene regulatory regions of DNA are meant. In addition to promoter regions the term encompasses operator regions more distant from the gene as well as nucleic acid sequences that influence the expression of a gene, such as cis-elements, enhancers or silencers. The term "promoter region" within the sense of the invention refers to a nucleotide sequence on the DNA allowing a regulated expression of a gene. In this case the promoter region allows regulated expression of the nucleic acid encoding for Vika (or Panto or Nigri respectively).

The promoter region is located at the 5'-end of the gene and thus before the RNA coding region. Both, bacterial and eukaryotic promoters are applicable for the invention.

In a method according to the invention, the vox sites (or pox sites or nox sites respectively) are either included in the cell or introduced into the cell, preferably by recombinant techniques. This preferred method according to the invention further includes the steps of introducing into a cell the following nucleic acids:
a) a first nucleic acid (first recognition site, first vox site or first pox site or first nox site respectively) comprising a nucleic acid sequence according to or reverse complementary to SEQ ID No. 2 (or SEQ ID No. 36 or 38 respectively); or a nucleic acid sequence that is a functional mutant thereof;
b) a second nucleic acid (second recognition site, second vox site or second pox site or second nox site respectively) comprising a nucleic acid sequence identical or reverse complementary to the nucleic acid sequence of the first nucleic acid (first recognition site).

In a preferred method according to the invention, a nucleic acid encoding for the Vika (or Panto or Nigri respectively), protein and one or two, preferably two, vox sites (or pox or nox sites respectively), are introduced into the cell. This method includes the following steps:
introducing into a cell the following nucleic acids:
  i) a nucleic acid encoding for Vika (or Panto or Nigri respectively), wherein the nucleic acid is introduced into the DNA such, that a regulatory nucleic acid sequence (preferably a promoter region) controls the expression of the nucleic acid encoding for Vika (or Panto or Nigri respectively),
  ii) a nucleic acid (first recognition site, first vox site or first pox site or first nox site respectively) comprising a nucleic acid sequence according to or reverse complementary to SEQ ID No. 22 (or SEQ ID No. 36 or 38 respectively); or a nucleic acid sequence that is a functional mutant thereof;
  iii) a nucleic acid (second recognition site, second vox site or second pox site or second nox site respectively) comprising a nucleic acid sequence identical or reverse complementary to the nucleic acid sequence defined in ii) (nucleic acid sequence of the first recognition site), and
activating the regulatory nucleic acid sequence (preferably the promoter region) to induce expression of the first nucleic acid for the synthesis of the protein with recombinase activity.

By this preferred method according to the invention, the nucleic acid sequence encoding for Vika (or Panto or Nigri respectively), is introduced into a cell and at least two recognition sizes (vox sites or pox sites or nox sites respectively) are introduced into the genomic or episomal DNA of the cell. The steps i) to iii) can be performed in arbitrary order.

The introduction of the nucleic acids into the cells is performed using techniques of genetic manipulation known by a person skilled in the art. Among suitable methods are cell transformation bacterial cells and transfection or viral infection for mammalian cells, whereby a nucleic acid sequence encoding the protein is introduced into the cell as a component of a vector or part of virus-encoding DNA or RNA. The cell culturing is carried out by methods known to a person skilled in the art for the culture of the respective cells. Therefore, cells are preferably transferred into a conventional culture medium, and cultured at temperatures (preferably 35-38° C.) and in a gas atmosphere that is conducive to the survival of the cells.

The method according to the invention can be performed using eukaryotic and prokaryotic cells; preferred prokaryotic cells are bacterial cells. Preferred prokaryotic cells are cells of *Escherichia coli*. Preferred eukaryotic cells are yeast cells (preferably *Saccharomyces cerevisiae*), insect cells, non-insect invertebrate cells, amphibian cells, or mammalian cells (preferably somatic or pluripotent stem cells, including embryonic stem cells and other pluripotent stem cells, like induced pluripotent stem cells, and other native cells or established cell lines, including NIH3T3, CHO, HeLa, HEK293, hiPS). In case of human embryonic stem cells, cells are preferably obtained without destructing human embryos, e. g. by outgrowth of single blastomeres derived from blastocysts as described by (Chung 2008), by parthenogenesis, e. g. from a one-pronuclear oocyte as described by (Lin 2007) or by parthenogenetic activation of human oocytes as described by (Mai 2007). Also preferred are cells of a non-human host organism, preferably non-human germ cells, somatic or pluripotent stem cells, including embryonic stem cells, or blastocytes.

Further, the invention includes a nucleic acid comprising a nucleic acid sequence according to or reverse complementary to SEQ ID No. 2 (or SEQ ID No. 36 or SEQ ID No. 38), or a nucleic acid sequence that is a functional mutant thereof. A nucleic acid according to the invention comprises a maximum of 40, preferably 34, base pairs. This nucleic acid according to the invention includes the recognition site vox of the Vika protein (or the pox site of Panto or the nox site of Nigri respectively) used according to the invention. Further the invention includes a vector (also referred to herein as "reporter vector") comprising at least one nucleic acid comprising a nucleic acid sequence according to or reverse complementary to SEQ ID No. 2 (or SEQ ID No. 36 or SEQ ID No. 38), or a nucleic acid sequence that is a functional mutant thereof. In a preferred embodiment of the invention the vector comprises at least two vox-sites (or at least two pox sites or at least two nox sites respectively), i.e. at least two nucleic acids that independently of each other exhibit a nucleic acid sequence according to or reverse complementary to SEQ ID No. 2 (or SEQ ID No. 36 or SEQ ID No. 38), or a nucleic acid sequence that is a functional mutant thereof. Thereby the at least two vox-sites are preferably not located consecutively in the vector. Rather the at least two vox sites (or at least two pox sites or at least two nox sites respectively), are positioned such that they are flanking a DNA segment, that upon recognition of the vox sites by the Vika protein (or the pox sites by Panto or the nox sites by Nigri respectively), the DNA segment is either excised or inverted. Thereby the DNA segment can preferably contain a gene or a promoter region. As described above, the DNA segment is excised when it is flanked by two vox-sites of the same orientation (same nucleic acid sequence). An inversion of the DNA segment is catalyzed by the Vika protein (or Panto or Nigri respectively), when the DNA segment is flanked by two vox-sites (or pox sites or nox sites respectively), arranged in opposite orientations (i.e. comprise a nucleic acid sequence reverse complementary to one another).

The term "nucleic acids" as used herein includes not only deoxyribonucleic acids (DNA) and ribonucleic acids (RNA), but also all other linear polymers in which the bases adenine (A), cytosine (C), guanine (G) and thymine (T) or uracil (U) are arranged in a corresponding sequence (nucleic acid sequence). The invention also comprises the corresponding RNA sequences (in which thymine is replaced by uracil), complementary sequences and sequences with modified nucleic acid backbone or 3 or 5'-terminus. Nucleic acids in the form of DNA are however preferred.

The term reporter vector as used herein includes a plasmid, virus or other nucleic acid carriers, that comprise a nucleic acid sequence according to the invention by genetic recombination (recombinantly), e.g. by insertion or incorporation of said nucleic acid sequence. Prokaryotic vectors as well as eukaryotic vectors, for example artificial chromosomes, such as YAC (yeast artificial chromosomes), are applicable for the invention. Typically, the expression vector comprises an origin of replication, a promoter, as well as specific gene sequences that allow phenotypic selection of host cells comprising the reporter vector.

The invention also includes a nucleic acid that encodes for a protein with recombinase activity, preferably Vika (or Panto or Nigri respectively), wherein the protein preferably comprises an amino acid sequence exhibiting at least 70%, preferably at least 80%, preferably at least 90%, particularly preferred at least 95%, even more preferred at least 99% amino acid sequence identity to SEQ ID No. 1 (or SEQ ID No. 35 or 37 respectively). Particularly preferred is a nucleic acid encoding for the Vika protein (or Panto or Nigri respectively), used according to the invention with a nucleic acid sequence according to SEQ ID No. 1 (or SEQ ID No. 35 or 37 respectively). Preferably, the nucleic acid comprises a nucleic acid sequence exhibiting at least 70%, preferably at least 80%, preferably at least 90%, particularly preferred at least 95%, even more preferred at least 99% nucleic acid sequence identity to SEQ ID No. 3. Furthermore, the invention includes a vector comprising said nucleic acid according to the invention (encoding for the protein with recombinase activity).

The invention also includes the use of the nucleic acids or vectors according to the invention in a method according to the invention for producing a site-specific DNA recombination.

When a nucleic acid encoding for a Vika protein, in particular in the form of a vector according to the invention, and at least two vox-sites as recognition sites are introduced into a host cell, a site-specific recombination is catalyzed upon expression of the protein Vika by its recognition of the vox sites.

Similar when a nucleic acid encoding for a Panto or Nigri protein, in particular in the form of a vector according to the invention, and at least two pox-sites or nox-sites as recognition sites are introduced into a host cell, a site-specific recombination is catalyzed upon expression of the protein Panto or Nigri by its recognition of the pox sites or nox sites respectively.

Accordingly, the invention also includes an isolated host cell comprising the following recombinant DNA fragments:
- at least one, preferably at least two, nucleic acids according to the invention comprising a vox-site (preferably two nucleic acids according to the invention that include a vox-site, respectively, flank a further DNA segment) and/or a nucleic acid according to the invention encoding for a Vika protein or
- a vector according to the invention comprising at least two nucleic acids comprising a vox-site (preferably two nucleic acids according to the invention that include a vox-site, respectively, flank a further DNA segment) and/or a vector according to the invention comprising a nucleic acid encoding for a Vika-protein.

Alternatively, the invention includes an isolated host cell comprising the following recombinant DNA fragments:
- at least one, preferably at least two, nucleic acids according to the invention comprising a pox-site (preferably two nucleic acids according to the invention that include a pox-site, respectively, flank a further DNA segment) and/or a nucleic acid according to the invention encoding for a Panto protein or
- a vector according to the invention comprising at least two nucleic acids comprising a pox-site (preferably two nucleic acids according to the invention that include a pox-site, respectively, flank a further DNA segment) and/or a vector according to the invention comprising a nucleic acid encoding for a Panto-protein, or
- at least one, preferably at least two, nucleic acids according to the invention comprising a nox-site (preferably two nucleic acids according to the invention that include a nox-site, respectively, flank a further DNA segment) and/or a nucleic acid according to the invention encoding for a Nigri protein or
- a vector according to the invention comprising at least two nucleic acids comprising a nox-site (preferably two nucleic acids according to the invention that include a nox-site, respectively, flank a further DNA segment) and/or a vector according to the invention comprising a nucleic acid encoding for a Nigri-protein.

The invention concerns only those isolated host cells that comprise the above mentioned nucleic acids or vectors recombinantly and not naturally, i.e. by genetic modification of the host cell. In particular the invention does not include cells of the organism *Vibrio coralliilyticus* ATCC BAA-450 that naturally contain a nucleic acid sequence encoding for Vika and comprising the recognition site vox. Further, the invention does preferably not include cells of the organism *Pantoea* sp. aB or *Vibrio nigripulchritudo* that contain a nucleic acid sequence encoding for Panto or Nigri and comprising the recognition site pox or nox.

Particularly preferred are isolated host cells that contain both, a nucleic acid encoding for Vika and at least two vox-sites (which are either oriented in the same or in opposite direction). Further preferred are isolated host cells that contain both, a nucleic acid encoding for Panto and at least two pox-sites (which are either oriented in the same or in opposite direction) or encoding for Nigri and at least two nox-sites (which are either oriented in the same or in opposite direction).

A host cell within the sense of the invention is a naturally occurring cell or a (optionally transformed or genetically modified) cell line that comprises at least one vector according to the invention or a nucleic acid according to the invention recombinantly, as described above. Thereby, the invention includes transient transfectants (e.g. by mRNA injection) or host cells that include at least one expression vector according to the invention as a plasmid or artificial chromosome, as well as host cells in which an expression vector according to the invention is stably integrated into the genome of said host cell. The host cell is preferably selected from cells of prokaryotes and eukaryotes. Preferred prokaryotic cells are cells of *Escherichia coli*. Preferred eukaryotic cells are selected from yeast cells (preferably *Saccharomyces cerevisiae*), insect cells, non-insect invertebrate cells, amphibian cells, and mammalian cells (preferably embryonal stem cells, NIH3T3, CHO, HeLa, HEK293, hiPS). Embryonal stem cells derived by killing of human embryos are specifically excluded from the term "host cells" within the sense of the invention.

With the invention it is also possible to induce tissue-specific site-specific recombination in non-human host organisms, such as mammals. Therefore the invention also includes a non-human host organism comprising the following recombinant DNA fragments:
- at least one, preferably at least two, nucleic acids according to the invention comprising a vox-site (preferably two nucleic acids according to the invention that include a vox-site, respectively, flank a further DNA segment) and/or a nucleic acid according to the invention encoding for a Vika protein or a vector according to the invention comprising at least two nucleic acids comprising a vox-site (preferably two nucleic acids according to the invention that include a vox-site, respectively, flank a further DNA segment) and/or a vector according to the invention comprising a nucleic acid encoding for a Vika-protein; or at least one, preferably at least two, nucleic acids according to the invention comprising a pox or nox-site (preferably two nucleic acids according to the invention that include a pox-site or nox-site, respectively, flank a further DNA segment) and/or a nucleic acid according to the invention encoding for a Panto or Nigri-protein or a vector according to the invention comprising at least two nucleic acids comprising a pox-site or nox-site (preferably two nucleic acids according to the invention that include a a pox-site or nox-site, respectively, flank a further DNA segment) and/or a vector according to the invention comprising a nucleic acid encoding for a Panto or Nigri-protein.

Explicitly included are non-human host organisms that only comprise a recombinant nucleic acid encoding for a Vika protein or Panto or Nigri protein respectively (and that do not comprise a nucleic acid including a vox site or pox site or nox site respectively). Furthermore, the invention includes non-human host organisms that only comprise at least one, preferably at least two, vox-sites or pox-sites or nox-sites respectively (and that do not comprise a nucleic acid encoding for a Vika protein or Panto or Nigri protein respectively). In that case, at least two vox sites (or pox site or nox site respectively), preferably flank another DNA segment. Upon cross-breeding of two non-human host organisms, wherein a first host organism comprises a recombinant nucleic acid encoding for a Vika protein (or Panto or Nigri protein respectively) and a second host organism comprises at least two recombinant vox-sites (or pox site or nox site respectively) and preferably flanking a further DNA segment, the offspring includes host organisms expressing Vika (or Panto or Nigri respectively) and further including the recognition sites vox (or pox or nox respectively), so that a site-specific DNA-recombination, like a tissue-specific conditional knock-out, is possible.

Non-human host organisms comprise a vector according to the invention or a nucleic acid according to the invention as described above that is, respectively, stably integrated into the genome of the host organism or individual cells of the host organism. Preferred host organisms are plants, invertebrates and vertebrates, particularly *Bovidae*, *Drosophila melanogaster*, *Caenorhabditis elegans*, *Xenopus laevis*, medaka, zebrafish, or *Mus musculus*, or embryos of these organisms.

The invention also includes a method for providing a non-human host organism, comprising the following steps:

providing a first non-human host organism comprising a nucleic acid encoding for a Vika protein (preferably comprising a nucleic acid sequence exhibiting at least 70%, preferably at least 80%, preferably at least 90%, particularly preferred at least least 95%, even more preferred at least 99% nucleic acid sequence identity to SEQ ID No. 3), providing a second non-human host organism comprising at least two nucleic acids, the nucleic acid sequence of which is independently from each other comprising a vox site (a nucleic acid sequence according to SEQ ID No. 2) or a nucleic acid sequence reverse complementary thereto or a nucleic acid sequence that is a functional mutant of the aforementioned nucleic acid sequences, wherein the at least two nucleic acids preferably flank another DNA segment (in particular a gene or a promoter region), cross-breeding of the first and the second non-human host organism and from the offspring obtained thereby selecting the non-human host organisms that comprise a nucleic acid encoding for a Vika protein and at least two nucleic acids, the nucleic acid sequence of which is independently from each other comprising a nucleic acid sequence according to SEQ ID No. 2 or a nucleic acid sequence reverse complementary thereto or a nucleic acid sequence that is a functional mutant of the aforementioned nucleic acid sequences.

Alternatively, the invention includes a method for providing a non-human host organism, comprising the following steps:

providing a first non-human host organism comprising a nucleic acid encoding for a Panto protein or a Nigri protein, providing a second non-human host organism comprising at least two nucleic acids, the nucleic acid sequence of which is independently from each other comprising a pox site (a nucleic acid sequence according to SEQ ID No. 36) or a nox site (a nucleic acid sequence according to SEQ ID No. 38) or a nucleic acid sequence reverse complementary thereto or a nucleic acid sequence that is a functional mutant of the aforementioned nucleic acid sequences, wherein the at least two nucleic acids preferably flank another DNA segment (in particular a gene or a promoter region), cross-breeding of the first and the second non-human host organism and from the offspring obtained thereby selecting the non-human host organisms that comprise a nucleic acid encoding for a Panto or Nigri protein and at least two pox sites (in case of Panto, the nucleic acid sequence of which is independently from each other comprising a nucleic acid sequence according to SEQ ID No. 36 or a nucleic acid sequence reverse complementary thereto or a nucleic acid sequence that is a functional mutant of the aforementioned nucleic acid sequences) or two nox sites (in case of Nigri, the nucleic acid sequence of which is independently from each other comprising a nucleic acid sequence according to SEQ ID No. 38 or a nucleic acid sequence reverse complementary thereto or a nucleic acid sequence that is a functional mutant of the aforementioned nucleic acid sequences).

The invention provides a novel recombinase system suitable for producing a site-specific recombination in cells of various cell types. Thereby, a diverse range of genetic manipulations can be realized, particularly rearrangements of the DNA fragments flanked by vox sites (or pox sites or nox sites respectively) in same orientation (excision), opposite orientation (inversion) or when one vox site (or pox site or nox site respectively) is present on each of two DNA molecules with one if it being in circular form in any orientation (integration). Exemplary manipulations are the excision of a DNA segment that is flanked by two vox-sites (or pox sites or nox sites respectively) oriented in the same direction mediated by the Vika (or Panto or Nigri) recombinase. Amongst others, the recombinase systems according to the invention, in particular the Vika/vox system, provides the possibility to excise a vox-flanked (or pox-flanked or nox-flanked) stopper DNA fragment which is located 5' of the gene and 3' of the corresponding to the gene promoter. Without recombination the stopper sequence prevents gene expression, whereas upon recombinase-mediated (preferably Vika-mediated) excision of the stopper via two flanking recognition sites (preferably vox sites) the gene is located to the proximity of the promoter and therefore is expressed. Different types of promoter regions that regulate the expression of the recombinase (preferably Vika) allow, inter alia, conditional DNA recombination, when for example a tissue or organism-specific or inducible promoter region is used to express the recombinase (preferably Vika).

For the recombinase systems according to the invention, in particular the Vika/vox system, no cross-reactivity with other recombinase systems was observed. Therefore, the recombinase systems according to the invention, in particular the Vika/vox system, are applicable for use in combination with other recombinase systems and becomes a particular valuable tool for genetic experiments where multiple recombinases are required simultaneously or sequentially. In bacterial cells, in particular in *E. coli*, a similar level of activity compared to the Cre/loxP system could be demonstrated. In *E. coli*, the recombinase systems according to the invention, in particular the Vika/vox system, showed a significantly higher activity than the VCre/VloxP system. In addition, the recombinase systems according to the invention, in particular the Vika/vox system, is highly effective and specific in mammalian cells as well. In human and mouse cells Vika carries out site-specific recombination on vox-sites. In mammalian cells Vika has shown comparable activity to Cre and superior compared to VCre. Furthermore, the inventors demonstrate that Vika does not recombine pseudo-vox-sites from human or mouse genomes. As a consequence, and in contrast to Cre, there is no observed reduction in proliferation or observed cytotoxicity upon overexpression of Vika in these cells. Therefore, the recombinase systems according to the invention, in particular the Vika/vox system, is advantageous especially for those applications in higher organisms when by using conventional SSRs such as the Cre/lox system cytotoxicity is observed.

Due to its efficiency in a variety of cell types the recombinase systems according to the invention, in particular Vika/vox, can be used in particular for producing site-specific DNA recombination in cells in which other recombinase systems were shown to only achieve poor results. For example, one of the most widely used recombinase system Cre/loxP has limited application in some model organisms such as *Caenorhabditis elegans*, supposedly due to the presence of loxP-like nucleic acid sequences being naturally present in the genome of *C. elegans*. The inventors have shown that there is a significantly lower number of vox-like sequences for potential targeting by Vika in the genome of *C. elegans*. Therefore, recombination activity of Vika/vox in *C. elegans* is likely to be superior to Cre/loxP.

It was demonstrated by the inventors that only low numbers of so-called pseudo-recognition sites (pseudo-vox sites) of Vika are present in the human and mouse genome. The number of pseudo-vox sites is markedly lower than the number of pseudo-loxP sites (pseudo-recognition sites of Cre) in the mouse and human genome. It was shown, that Vika does not recombine on pseudo-vox sites originating from human and mouse genomes. On the contrary, Cre showed prominent activity on human and mouse pseudo-loxP sites.

Additionally, the inventors demonstrated in in vitro experiments, that stable expression of Vika does not cause cytopathic effects in human and mouse cells and that stable expression of Vika does not lead to increased DNA damage.

The object of the invention is also solved by the use of a protein with recombinase activity, wherein the protein comprises an amino acid sequence exhibiting at least 70%, preferably at least 80%, preferably at least 90%, particularly preferred at least 95%, even more preferred at least 99% amino acid sequence identity to one of the amino acid sequences according to SEQ ID No. 19, 21, 23, 25, 27, 29, 31 or 33 catalyze a site-specific DNA recombination. The aforementioned site-specific recombinase is used for site-specific DNA recombination at, preferably two, recognition sites that are identical or reverse complementary to each other, wherein at least one recognition site comprises a nucleic acid sequence according to or reverse complementary to the nucleic acid sequence according to SEQ ID No. 20, 22, 24, 26, 28, 30, 32 or 34, respectively; or a nucleic acid sequence that is a functional mutant thereof.

The object of the invention is also solved by the use of a protein with recombinase activity, wherein the protein comprises an amino acid sequence exhibiting at least 70%, preferably at least 80%, preferably at least 90%, particularly preferred at least 95%, even more preferred at least 99% amino acid sequence identity to one of the amino acid sequences according to SEQ ID No. 35 to catalyze a site-specific DNA recombination. The aforementioned site-specific recombinase is used for site-specific DNA recombination at, preferably two, recognition sites that are identical or reverse complementary to each other, wherein at least one recognition site comprises a nucleic acid sequence according to or reverse complementary to the nucleic acid sequence according to SEQ ID No. 36, respectively; or a nucleic acid sequence that is a functional mutant thereof.

The object of the invention is also solved by the use of a protein with recombinase activity, wherein the protein comprises an amino acid sequence exhibiting at least 70%, preferably at least 80%, preferably at least 90%, particularly preferred at least 95%, even more preferred at least 99% amino acid sequence identity to one of the amino acid sequences according to SEQ ID No. 37 to catalyze a site-specific DNA recombination. The aforementioned site-specific recombinase is used for site-specific DNA recombination at, preferably two, recognition sites that are identical or reverse complementary to each other, wherein at least one recognition site comprises a nucleic acid sequence according to or reverse complementary to the nucleic acid sequence according to SEQ ID No. 38, respectively; or a nucleic acid sequence that is a functional mutant thereof.

The proteins with recombinase activity and recognition sites are used in the following combination (table 1). Derivatives of the respective protein with amino acid sequence identities of at least 70%, preferably at least 80%, preferably at least 90%, particularly preferred at least 95%, even more preferred at least 99% and recognition sites with a nucleic acid sequence that is reverse complementary to the indicates nucleic acid sequence as well as their functional mutants are also included. It is preferred to use the indicated proteins with recombinase activity on wild type recognition sites or recognition sites with a nucleic acid sequence reverse complementary thereto.

TABLE 1

| Gen bank accession number of protein; Organism | Amino acid sequence of protein (site specific recombinase) | Nucleic acid sequence of wild type recognition site |
|---|---|---|
| EGU56467.1 *Vibrio tubiashii* ATCC 19109 | SEQ ID No. 19 | SEQ ID No. 20 |
| YP_003065675.1 *Methylobacterium extorquens* DM4 | SEQ ID No. 21 | SEQ ID No. 22 |

TABLE 1-continued

| Gen bank accession number of protein; Organism | Amino acid sequence of protein (site specific recombinase) | Nucleic acid sequence of wild type recognition site |
|---|---|---|
| YP_003280920.1 Streptomyces sp. W9 | SEQ ID No. 23 | SEQ ID No. 24 |
| ZP_06822377.1 Streptomyces sp. SPB74 | SEQ ID No. 25 | SEQ ID No. 26 |
| NP_395953.2 Agrobacterium tumefaciens str. C58 plasmid At | SEQ ID No. 27 | SEQ ID No. 28 |
| YP_666181.1 Chelativorans sp_BNC1 plasmid 3 | SEQ ID No. 29 | SEQ ID No. 30 |
| YP_957160.1 Marinobacter aquaeolei VT8 plasmid pMAQU02 | SEQ ID No. 31 | SEQ ID No. 32 |
| NP_943161.1 Pseudomonas sp. ND6 plasmid pND6-1 | SEQ ID No. 33 | SEQ ID No. 34 |
| WP_008927019.1 Pantoea sp. aB | SEQ ID No. 35 | SEQ ID No. 36 |
| YP_004250912.1 Vibrio nigripulchritudo | SEQ ID No. 37 | SEQ ID No. 38 |

The invention is further based on the finding of the inventors that each of the proteins listed in table 1 in column 2, shows a Cre recombinase-like activity and recognizes recognition sites as indicated in table 1 in column 3. The organisms from which each of the site-specific recombinases is derived from are also indicated in table 1 (column 1). All of the proteins with recombinase activity listed in table 1 show a low amino acid sequence identity to Cre recombinase.

The invention further relates to a method for producing a site-specific DNA-recombination by contacting a protein with recombinase activity with the indicated recognition sites.

The invention also includes nucleic acids exhibiting a length not more than 40 base pairs, each nucleic acid comprising a nucleic acid sequence according to SEQ ID No. 20, 22, 24, 26, 28, 30, 32 or 34 or SEQ ID No. 36 or SEQ ID No.38, a nucleic acid sequence that is a functional mutant thereof or a nucleic acid sequence reverse complementary thereto.

Additionally, the invention relates to vectors comprising said nucleic acid sequences, preferably at least one, even more preferred at least two identical or reverse complementary nucleic acid sequences.

In an even further embodiment the invention relates to vectors comprising a nucleic acid encoding for a protein with recombinase activity wherein the protein comprises an amino acid sequence exhibiting at least 70%, preferably at least 80%, preferably at least 90%, particularly preferred at least 95%, even more preferred at least 99% amino acid sequence identity to SEQ ID No. 19, 21, 23, 25, 27, 29, 31 or 33 or SEQ ID No. 35.

The use of any of the vectors according to the invention in a method for producing a site-specific DNA-recombination is also included in the invention.

Further, the invention includes an isolated host cell or an isolated host organism comprising
  at least one, preferably at least two, nucleic acids according to the invention comprising a recognition site as defined above (preferably two nucleic acids according to the invention that include a recognition site, respectively, flank a further DNA segment) and/or a nucleic acid according to the invention encoding for a protein with recombinase activity, as defined above, or
  a vector according to the invention comprising at least two nucleic acids comprising a recognition site as defined above (preferably two nucleic acids according to the invention that include a recognition site, respectively, flank a further DNA segment) and/or a vector according to the invention comprising a nucleic acid encoding for a protein with recombinase activity as defined above.

The embodiments of the invention that are described above in detail for site-specific recombination with Vika on vox-sites and Panto on pox sites and Nigri on nox sites are also included within the invention for site-specific recombination with one of the above mentioned site-specific recombinases on their recognition sites.

For each of the proteins with recombinase activity, the inventors identified numerous putative recognition sites with a lox-like structure in the organism wherefrom the recombinase was derived. Upon extensive studies only one thereof, the indicated respective wild type recognition site, turned out to be the actual recognition site of the indicated protein with recombinase activity. By expression of the nucleic acid sequence encoding for the site-specific recombinase in E. coli, the recombinase protein could be successfully obtained and its recombinase activity and specify for the respective wild type recognition site could be demonstrated. It was shown that the indicated proteins with recombinase activity do not cross react with other known recombinase systems and are superior in the activity compared to some of the known recombinase systems, at least in certain cell types.

BRIEF DESCRIPTION OF THE DRAWINGS

The invention is further illustrated by the following figures and examples without being limited to these.

FIG. 1 Amino acid sequence alignment of the sequences of Vika (SEQ ID No. 1) and Cre (SEQ ID No. 4). Residues from Cre-recombinase known to be essential for DNA interaction are highlighted, as well as their analogues in the recombinase Vika, with catalytic residues in black, DNA contacting residues underlined.

FIG. 3 Nucleic acid sequence alignment of the recognition sites loxP (SEQ ID No. 5), rox (SEQ ID No. 9), vox (SEQ ID No. 2) and vloxP (SEQ ID No. 11).

FIG. 4A A drawing providing a determination of specificity of the Vika/vox system and analysis of potential cross-reactivities between Vika/vox and other recombinase systems when performing DNA recombination in E. coli. (−) and (+) indicate the addition of 100 µg/ml of L (+)-arabinose for the induction of DNA recombination. The bands for the non-recombinant plasmids are represented as two triangles, the recombinant plasmids are represented by one triangle, M . . . DNA marker. Specificity of the indicated site-specific DNA recombinases Cre, Dre, VCre and Vika on vox sites.

FIG. 4B A drawing providing specificity of the indicated site-specific DNA recombinases at recognition sites loxP, rox and VloxP.

EXAMPLE 1: 3D MODEL OF A PROTEIN WITH RECOMBINASE ACTIVITY (VIKA)

Figure 2A:
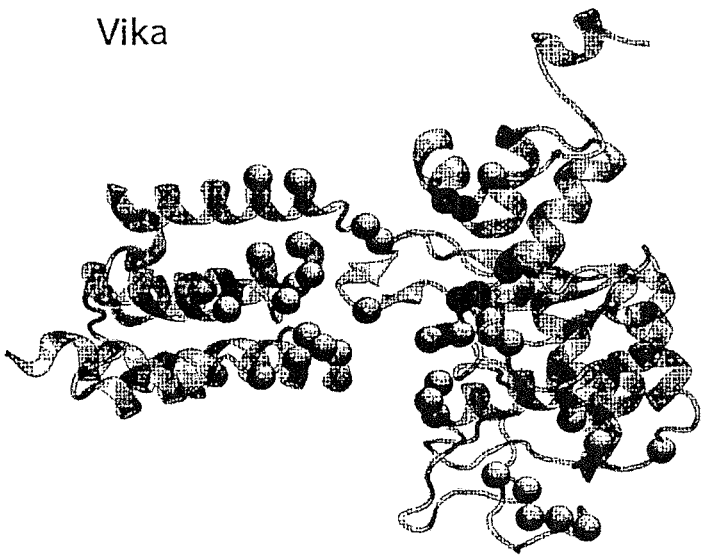
FIG. 2A Three-dimensional structure of the recombinase Vika obtained by 3D-modelling.
Figure 2B:
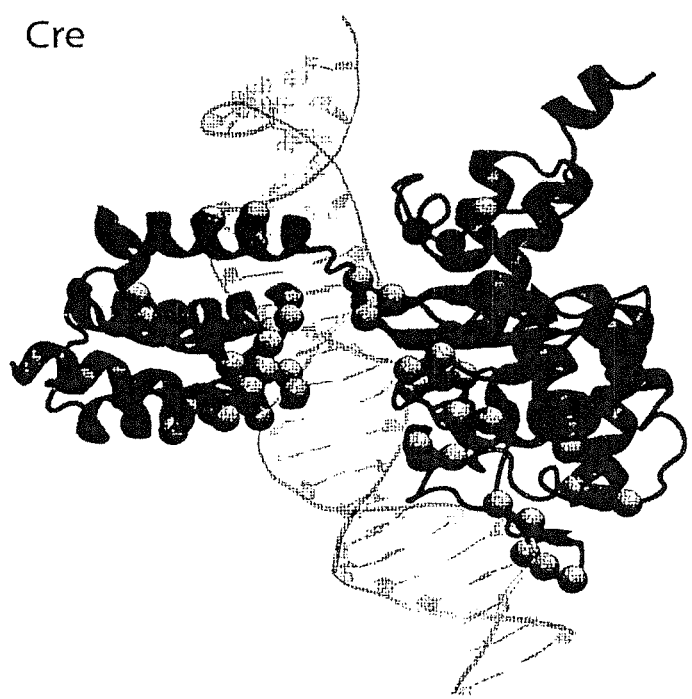
FIG. 2B A drawing showing the crystal structure of Cre recombinase. Residues from Cre-recombinase known to be essential for DNA interaction are highlighted, as well as their analogues in the recombinase Vika, with catalytic and contacting residues.

Vika is annotated in NCBI under number ZP_05884863 and originates from the gram-negative bacterium *Vibrio coralliilyticus* ATCC BAA-450. Vika exhibits a low amino acid sequence identity of 27.7% to Cre recombinase (50.2% sequence similarity) (FIG. 1). In order to analyze the binding properties of the protein ZP_05884863 compared to Cre recombinase, a 3D atom model was developed using the crystal structure of Cre recombinase as a template (FIG. 2). The resulting 3D model showed an RMSD (root-mean-square deviation) of 2.4±0.3 Å when compared to the Cre template. From this data a strong structural similarity between these two proteins can be concluded. It is apparent from the 3D model that five catalytically important residues known from Cre recombinase are conserved in Vika.

In extensive experiments six putative recognition sites from the genome of *Vibrio coralliilyticus* ATCC BAA-450 were identified by the inventors. Therefrom, the nucleic acid herein referred to as vox-site was identified to be the recognition site of Vika. The vox site is a 34 bp DNA sequence consisting of two inverted repeats, comprising about 50% sequence homology to loxP and 55% to VloxP and about 33% sequence homology to rox (FIG. 3). The nucleic acid sequence of the vox-site is presented in SEQ ID No. 2.

EXAMPLE 2: RECOMBINASE ACTIVITY OF VIKA AND RECOGNITION OF VOX-SITES IN E. COLI

To verify whether the protein Vika exhibits recombinase activity and to verify that vox is its recognition site, a nucleic acid encoding for Vika was cloned into an E. coli recombination reporter plasmid that comprised two vox-sites of the same orientation. The recombination reporter plasmid was based on the plasmid pEVO (Buchholz and Stewart, 2001), in which the recombinase was inserted via a BsrGI and XbaI cleavage site. In the plasmid, the two vox-sites flanked an approximately 1 kb DNA segment that was excised by DNA-recombination. DNA recombination was induced by the addition of L (+)-arabinose. It was shown that Vika mediated a DNA recombination at vox-sites (FIG. 4A, right). Therefore, it could be shown that the Vika/vox system is a recombinase system applicable in E. coli cells.

In further experiments, the activity of Vika/vox in different cell types as well as possible cross-reactions with other recombinase systems were assessed.

EXAMPLE 3: NO CROSS-REACTIVITY WITH OTHER RECOMBINASE SYSTEMS—NO RECOGNITION OF OTHER LOX SITES BY VIKA AND NO RECOGNITION OF VOX SITES BY OTHER RECOMBINASES

To assess whether Vika recognizes the recognition sites of known recombinase systems, in particular loxP, VloxP and rox, the nucleic acid sequence encoding for Vika was cloned into *E. coli* recombination reporter plasmids comprising the aforementioned recognition sequences, respectively. The recombination reporter plasmids were based on the plasmid pEVO (Buchholz and Stewart, 2001), into which the recombinase was inserted via a BsrGI and XbaI cleavage sites.

In a reporter plasmid, an approximately 1 kb long DNA portion was flanked by two lox sites of the same orientation (either loxP, VloxP or rox). Thereby upon site-specific DNA recombination (induced by addition of L (+)-arabinose) the 1 kb DNA segment was excised from the plasmid. FIG. 4B shows that the recombinase Vika is not applicable to produce a DNA recombination at any of the lox sites loxP, VloxP and rox.

Furthermore it was assessed whether other known recombinases can produce a site-specific recombination on vox sites. For this purpose, reporter plasmids, each containing Cre, Dre, VCre or Vika and further including two vox sites were transformed into *E. coli*. The results show that only Vika, but not Cre, Dre and VCre induce recombination at vox-sites (FIG. 4A). Further experiments using lacZ reporter assays confirmed the specificity of Vika to its recognition sites vox.

Therefore, Vika can be used in combination with other recombinase systems without causing cross-reactions.

EXAMPLE 4: ACTIVITY OF DIFFERENT RECOMBINASE SYSTEMS IN *E. COLI*

Figure 5:
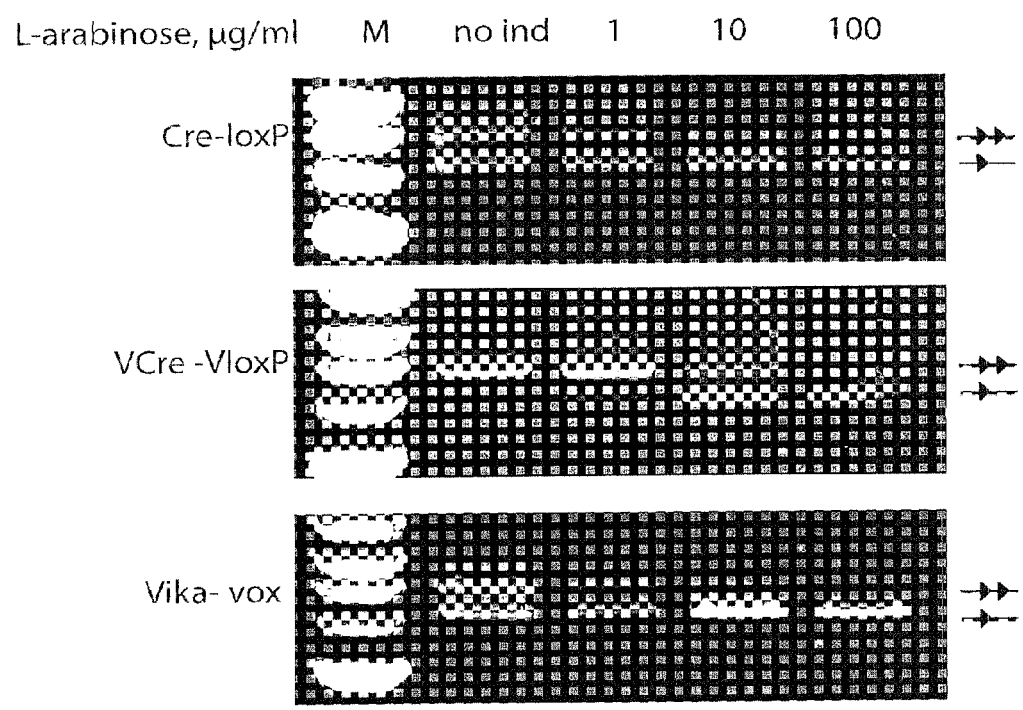
FIG. 5 Determination of recombination activity of the indicated recombination systems Cre/loxP, VCre/VloxP and Vika/vox in E. coli. The bands for the non-recombinant plasmids are represented as two triangles, the recombinant plasmids are represented by one triangle, M . . . DNA marker. Successful recombination events upon addition of various amounts of L (+)-arabinose for induction of DNA recombination are indicated: "no ind" . . . negative control without addition of L (+)-arabinose, further data show recombination upon addition of 1, 10, 100 µg/ml L (+)-arabinose as indicated.

The activity of the recombinase systems Vika/vox, Cre/loxP and VCre/VloxP was compared in *E. coli* cells. For this purpose recombination reporter plasmids as described in Example 2 or 3 that included the nucleic acid sequence encoding for the respective recombinase and two respective recognition sites of the same orientation were used. For a quantitative analysis, different concentrations of L (+)-arabinose were added in order to induce the DNA recombination: 0, 1, 10 and 100 µg/ml (FIG. 5).

Figure 6A:
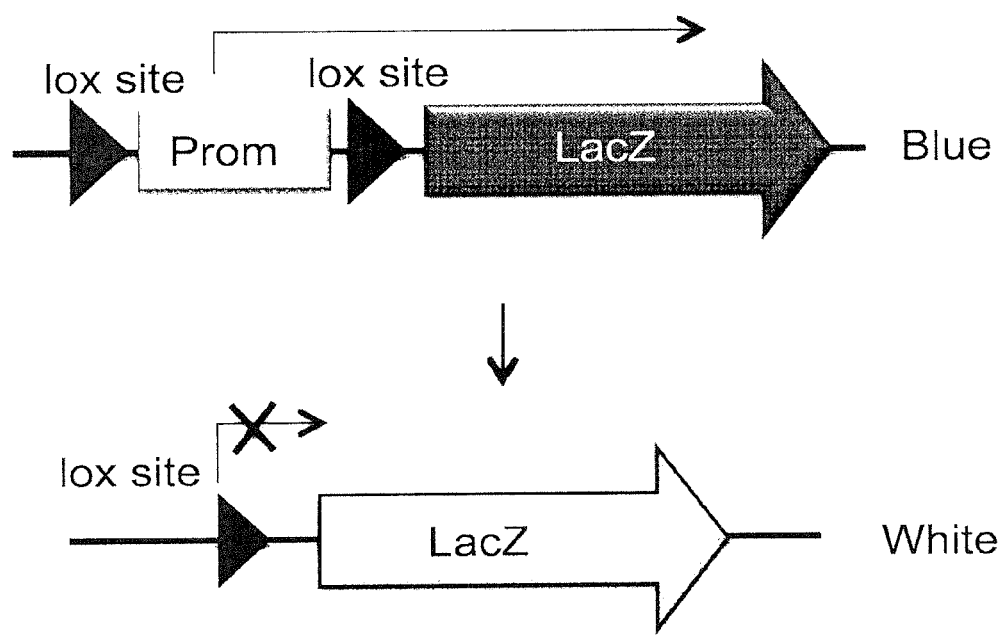
FIG. 6A A schematic representation for determination of the recombination activity of the indicated recombination systems Cre/loxP, VCre/VloxP and Vika/vox in E. coli using a lacZ reporter assay. The lacZ reporter assay; non-recombined plasmids express beta-galactosidase resulting in the formation of blue colonies when cultured on X-Gal-containing medium; in the recombined plasmids the promoter of the lacZ gene that was originally located between two recognition sequences was excised, thereby beta-galactosidase is not expressed, resulting in the formation of white colonies when cultured on X-Gal containing medium.
Figure 6B:
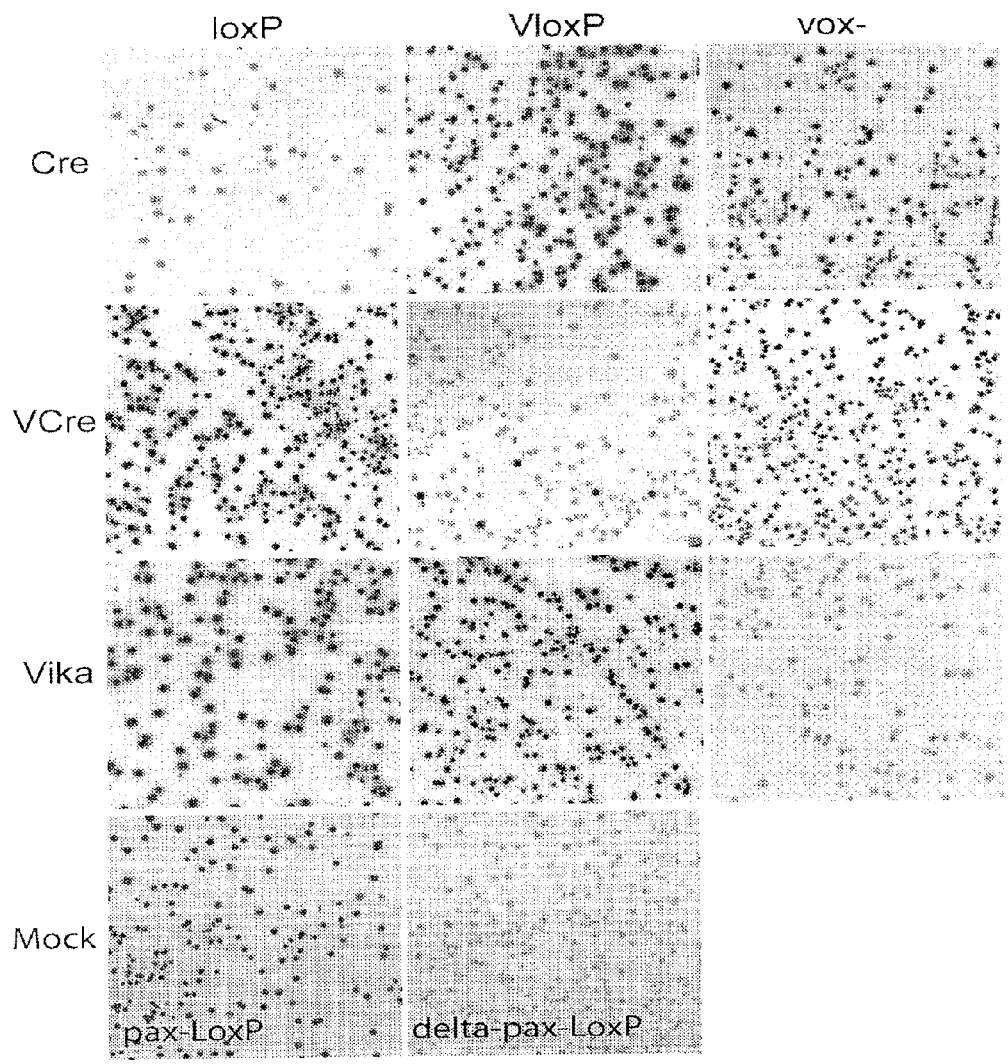
FIG. 6B Photographs showing specificity of Cre, VCre and Vika in LacZ-based assay. White colonies, signifying recombination, only appear when a recombinase is expressed together with its corresponding reporter. Positive controls for the non-recombined (pSVpaX), and recombined form of the reporter (pSVpaXΔ) is shown as Mock.

Further, in another approach, a lacZ reporter assay was used in order to compare the activities of the three above-mentioned recombinase systems. For this purpose, reporter plasmids were constructed by introducing two of the respective recognition sequences (vox, lox and VloxP) into a pSV-paXl vector ((Buchholz and Bishop, 2001), schematic representation in FIG. 6A). Plasmid DNA was isolated and introduced into DH5α cells by electroporation. The resulting cells were used in defined concentration and plated in the presence of ampicillin on X-gal containing plates. The number of white and blue colonies was counted (FIG. 6B).

In a further approach using two vectors comprising one recognition site (loxP, VloxP or vox), respectively, and the corresponding recombinases (Cre, VloxP, Vika) it was shown that only combinations of two identical target sites and their corresponding recombinases produced co-integrant plasmids.

EXAMPLE 5: ACTIVITY OF DIFFERENT RECOMBINASE IN MAMMALIAN CELLS

To assess out whether the Vika/vox system is active in cells other than the natural host cells and *E. coli*, recombinase activity was analyzed in human HeLa cells and compared with activities of the known recombinase systems Cre/loxP and VCre/VloxP.

Figure 7A:
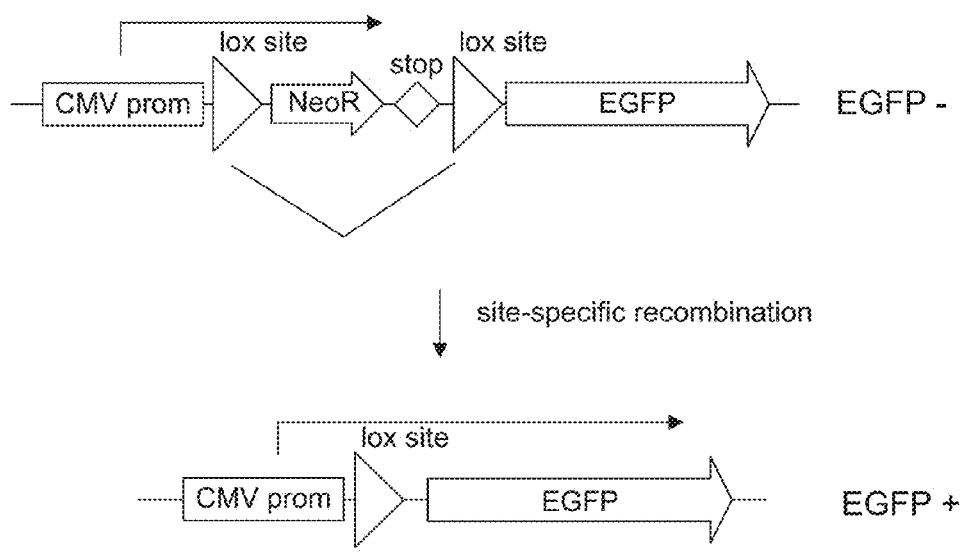
FIG. 7A A schematic representation with comparison of recombination activities of the indicated recombinase systems Cre/loxP, VCre/VloxP and Vika/vox in human HeLa cells. Schematic representation of the EGFP-based reporter assays. The non-recombined plasmids express the gene for neomycin resistance (NeoR). Upon DNA recombination, the neomycin cassette is removed so that the cytomegalovirus promoter (CMV prom), that was originally driving expression of the neomycin resistance gene, is located to the proximity of the EGFP gene induces its expression.
Figure 7B:
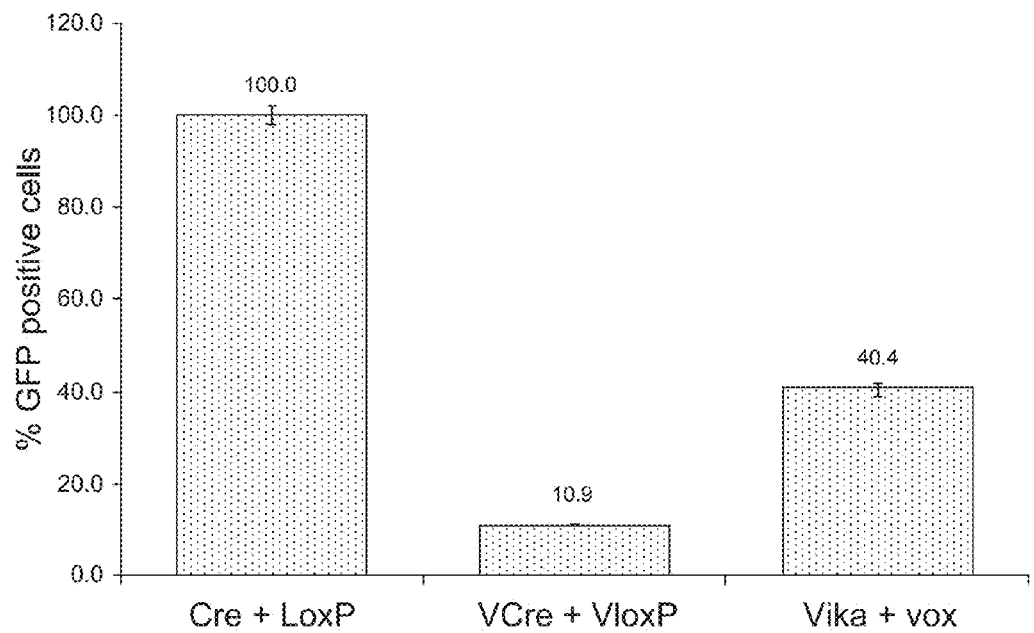
FIG. 7B is a graph of % GFP-positive cells resulting from the recombination assays for Cre, VCre and Vika in HeLa cells.
Figure 7C:
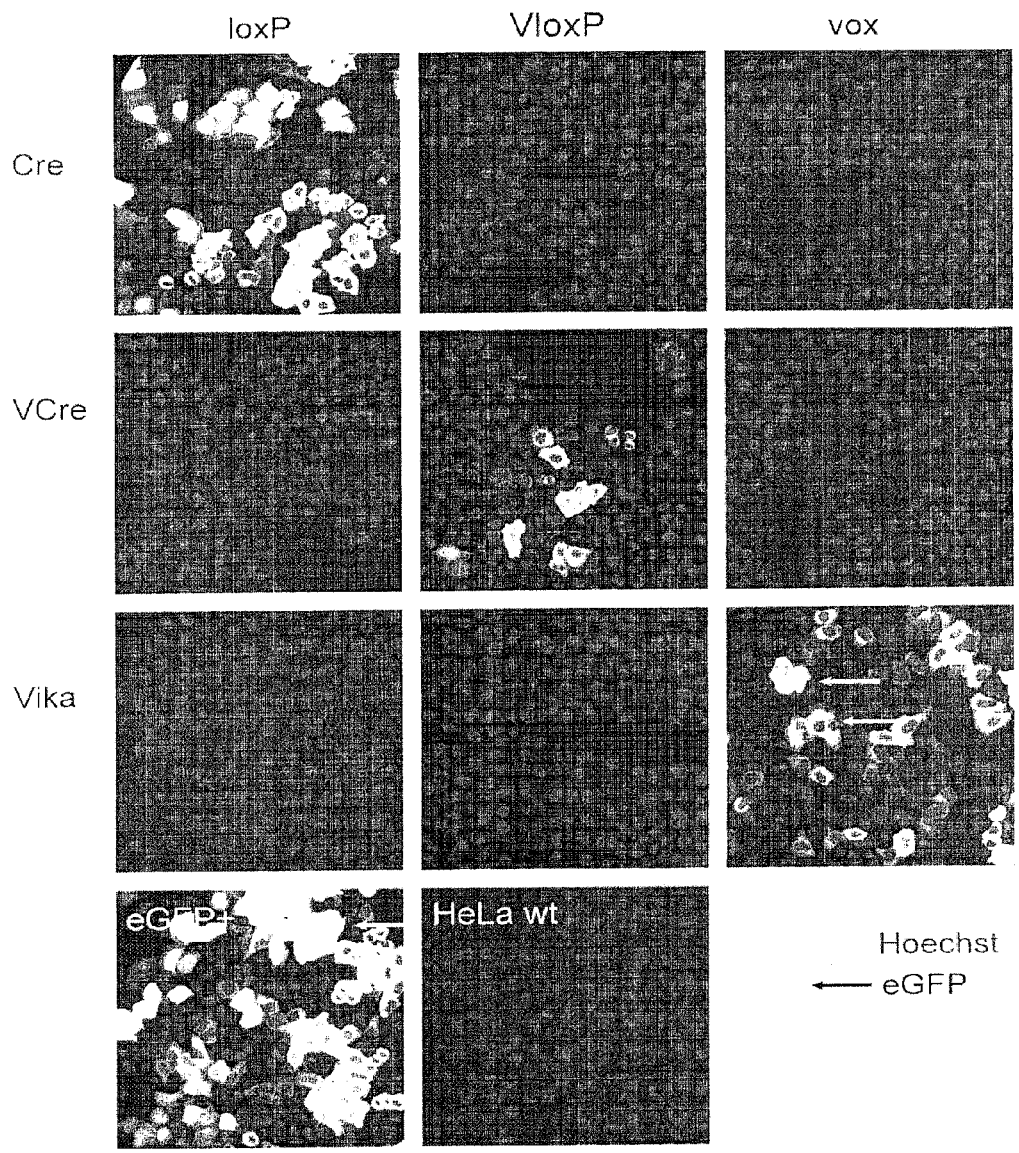
FIG. 7C is a fluorescence microscopic image of the recombination assays for Cre, VCre and Vika in HeLa cells.

For this purpose, HeLa cells were transfected with a reporter plasmid encoding for EGFP. The reporter plasmids were based on the plasmid pEGFP-X ((Buchholz and Bishop, 2001), schematic representation in FIG. 7A). A neomycin cassette was flanked by two of the respective recognition sites of the same orientation. Using this plasmid, cloning of the respective recognition sites into said plasmid, the reporter plasmids pRK5-loxP-EGFP, pRK5-VloxP-EGFP and pRK5-vox-EGFP were derived. HeLa cells were plated in 6-well plates with a cell number of $2\times10^5$ cells and cultured in cell culture medium (4.5 mg/ml glucose DMEM comprising 10% FBS and 100 U/ml penicillin/streptomycin). The reporter plasmids comprising the recognition sites (pRK5-loxP-EGFP, pRK5-VloxP-EGFP and pRK5-vox-EGFP) were co-transfected into HeLa cells with the respective recombinase expression plasmid pNPK-NLS-Cre, pNPK-NLS-VCre and pNPK-NLS-Vika. Cells were cultured for 24 h. Subsequently, the cells were washed with PBS and fixed and examined using fluorescence microscopy (FIG. 7B, C).

It could be shown that the Vika/vox system is suitable for producing a DNA recombination in human HeLa cells and that it shows superior activity when compared to the known VCre/VloxP system.

EXAMPLE 6: ACTIVITY ON CRYPTIC CHROMOSOMAL SITE OF MOUSE AND HUMAN GENOMES

In order to investigate potential site-effects of Vika, pseudo-vox sites in the mouse and human genome were identified. In both species, lower overall numbers of pseudo-vox sites were uncovered than pseudo-loxP sites. Pseudo-vox sites that most closely resembled vox sites were tested experimentally. The nucleic acid sequences of the tested pseudo-vox sites correspond to the following SEQ ID No.:

voxCH18 (7 mutations): SEQ ID No. 12
voxCH21 (6 mutations): SEQ ID No. 13
voxCHX (6 mutations): SEQ ID No. 14
voxCMp92 (6 mutations): SEQ ID No. 15
voxCHp3 (6 mutations): SEQ ID No. 16

As a comparative example, recombination with Cre on two pseudo-loxP sites was examined. The nucleic acid sequences of the tested pseudo-loxP sites correspond to the following SEQ ID No.:

loxhXp22 (7 mutations): SEQ ID No. 17
loxM5 (5 mutations): SEQ ID No. 18\

Figure 8:
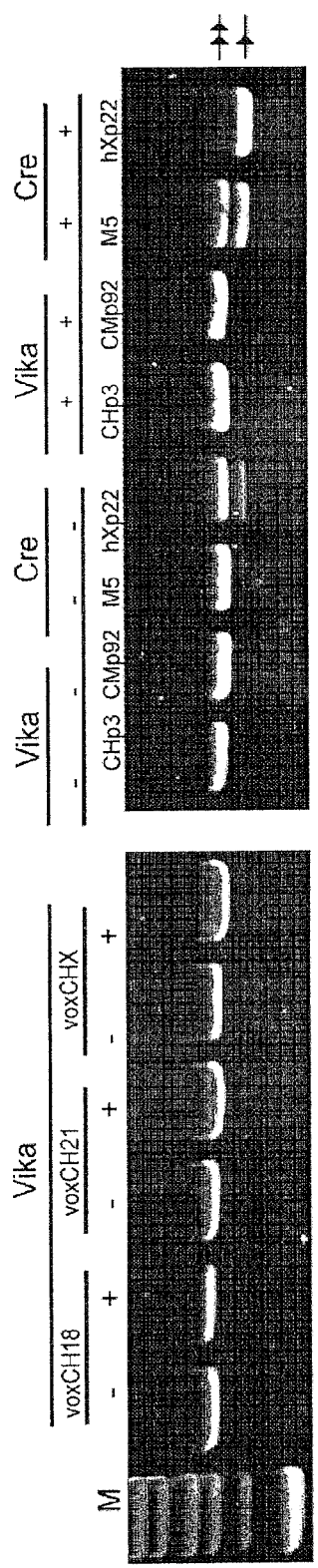
FIG. 8 Evaluation of genotoxicity of Vika. Recombination specificity of Vika and Cre on the respective cryptic human and mouse chromosomal target sites (see example 6). − and + indicates presence or absence of L(+)-arabinose (100 µg/ml) in the growth medium. Non-recombined and recombined plasmids are denoted as two triangles and one triangle, respectively. M, marker, 2-log DNA ladder, NEB.

It was demonstrated that Cre showed prominent activity on pseudo-loxP sites (FIG. 8) in *E. coli*. In contrast, Vika did not display measurable activity on pseudo-vox sites in these assays (FIG. 8).

EXAMPLE 7: PROLONGED CONSTITUTIVE EXPRESSION IN PRIMARY CELLS (MOUSE ES CELLS)

Figure 9:
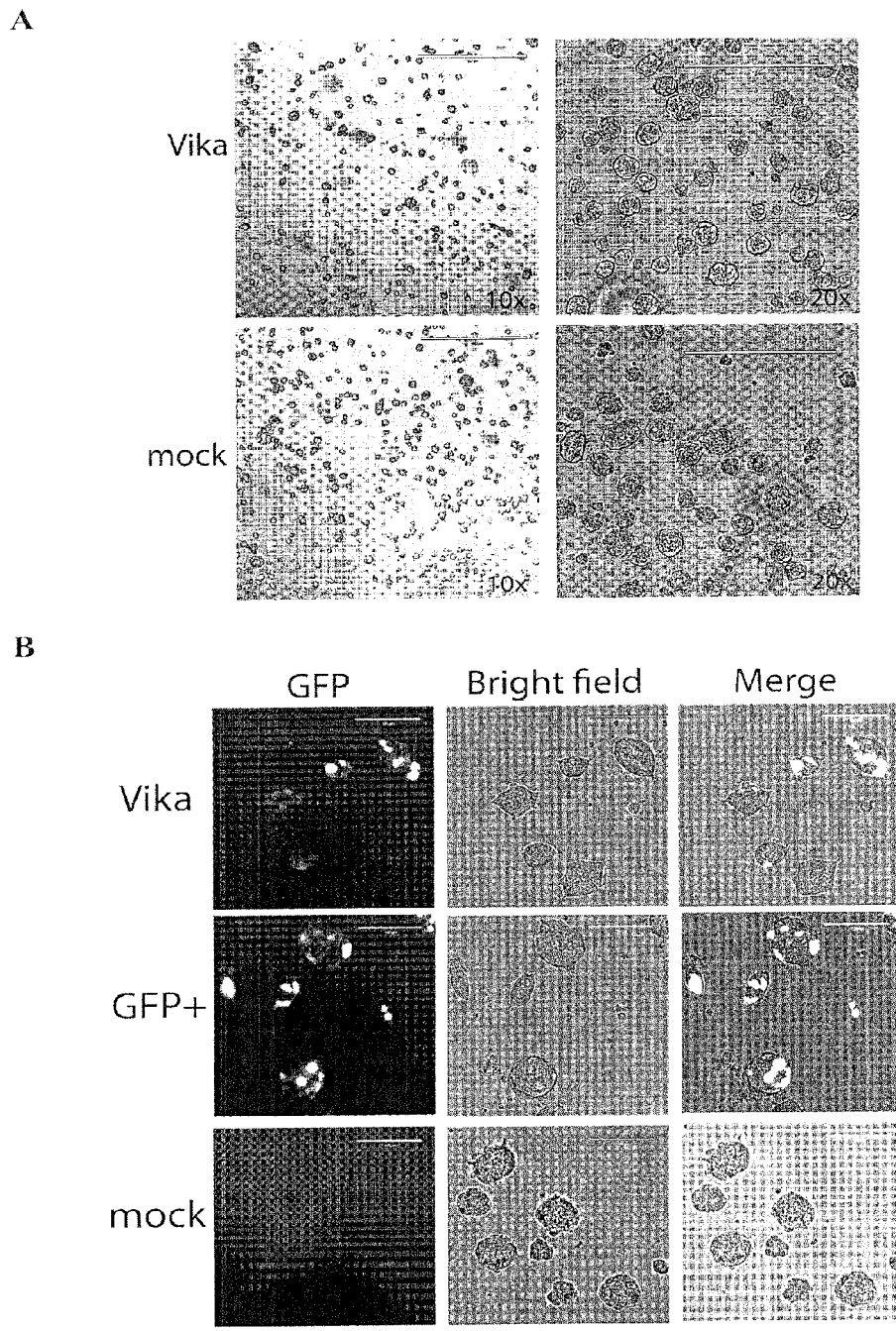
FIG. 9 Evaluation of prolonged expression of Vika in mouse ES cells. A) mouse ES cell line with stably integrated Vika recombinase after prolonged passaging (24 days). A representative photo of a clonal culture is depicted (brightfield image). B) Recombination activity of stably expressed Vika recombinase in mouse ES cell line. Images show cells 24 hours after transfection with vox-GFP reporter plasmid. Note the apparent Vika-mediated recombination signified through GFP expression. A control of the recombined reporter plasmid (GFP+) was transfected for detecting transfection efficiency.

In order to examine the influence of prolonged expression of Vika in primary cells, mouse ES cells stably expressing Vika were generated. No effect on cell growth and morphology was observed, indicating that Vika is active when selected for stable expression in mouse ES cells and is well tolerated (FIG. 9).

EXAMPLE 8: DNA DAMAGE EVALUATION BASED ON γ-H2AX ASSAY

Figure 10:
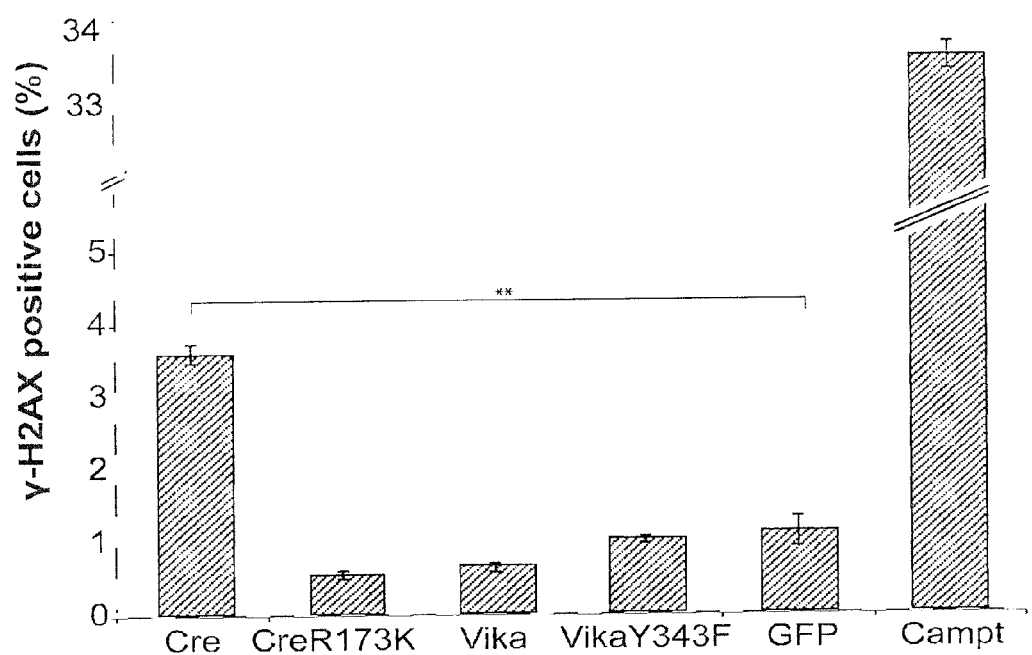
FIG. 10 Evaluation of DNA damage induction in mouse NIH3T3 cells by γ-H2AX assay 72 h after infection with indicated recombinase-expressing virus. Quantification of the γ-H2AX positive cells either infected with virus for respective recombinase expression or treated with campthothecin for 2 h. Statistically significant increase of γ-H2AX signals is indicated by asterisks. Error bars indicate standard deviation of the mean value. (** indicate p=0.01). n=3.

The potential impact of recombinase expression on DNA damage was examined. NIH3T3 cells were infected with GFP-bicistronic retroviral particles encoding Cre, Vika or controls. Three days post infection, γ-H2AX signals were investigated in fixed cells. Cre expression caused a marked increase in γ-H2AX signals signifying induction of DNA damage. In contrast, Vika had no influence on the amount of γ-H2AX counted (FIG. 10), indicating that Vika expression does not lead to increased DNA damage in these cells.

Figure 11:
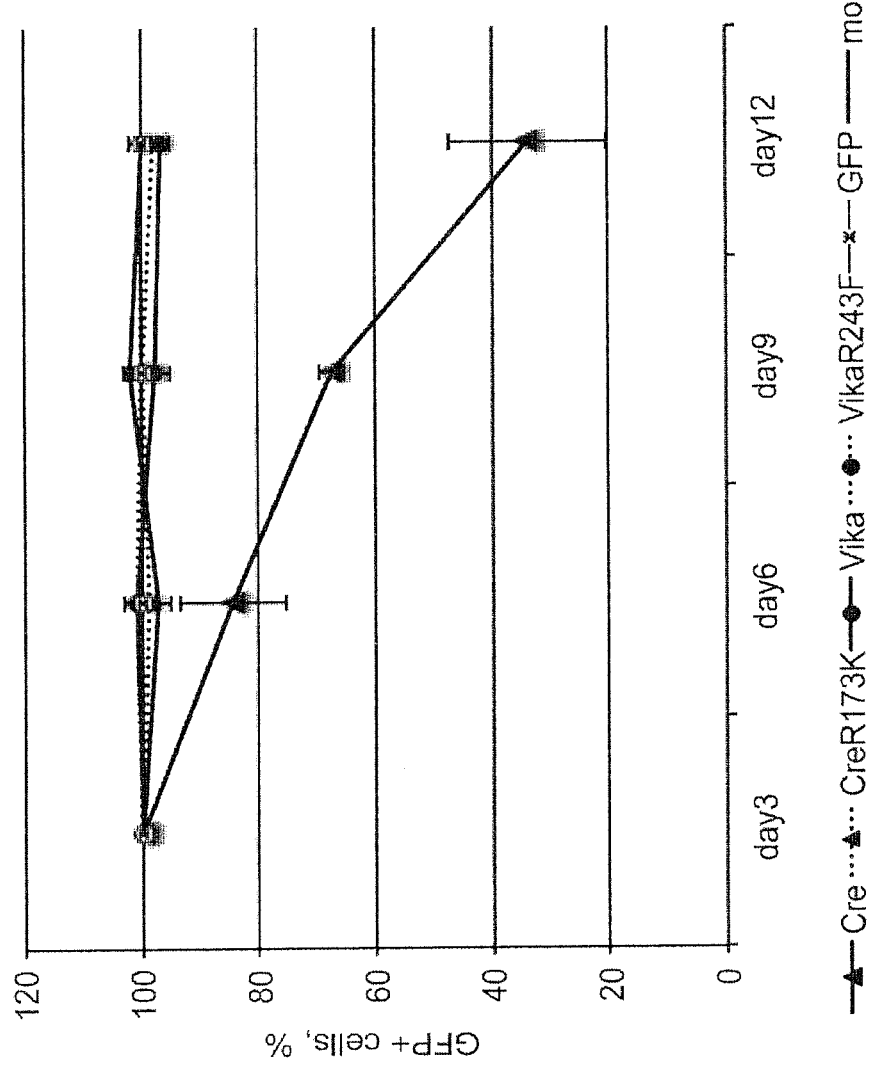
FIG. 11 Evaluation of cytotoxicity of Vika. Proliferation effects upon expression of indicated recombinases in mouse NIH3T3 cells. Cells were infected with bicistronic retroviruses expressing respective recombinase linked to GFP. Every 72 hours cells were analyzed by flow cytometry. Error bars indicate standard deviation of the mean value, n=2.

EXAMPLE 9: NO CYTOTOXIC EFFECT UPON HIGH-LEVEL EXPRESSION IN MOUSE CELLS, (RETROVIRAL EXPERIMENT). (FIG. 11)

The percentage of GFP-positive cells over time in the populations of example 8 was examined as an indicator for cytotoxicity. Cre expression led to a rapid decline of GFP positive cells in the population (that is consistent with previously published information). However, no decline in GFP positive cells was observed in Vika expressing cells (FIG. 11). These experiments demonstrate that high levels of Cre are cytotoxic, whereas Vika expression is well tolerated in the same setting.

EXAMPLE 10: RECOMBINASE ACTIVITY OF PANTO AND NIGRI ON POX AND NOX RECOMBINATION TARGET SITES IN E. COLI

Figure 12:
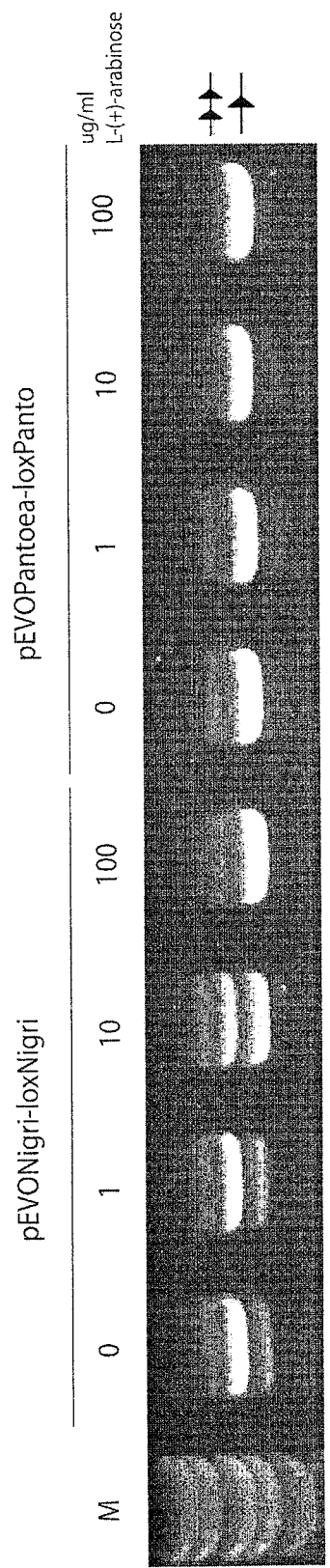
FIG. 12 Recombinase activity of Panto and Nigri on pox and nox recombination target sites in E. coli.

To verify whether the protein Panto and Nigri exhibit recombinase activity and to verify that pox and nox are corresponding recognition sites, a nucleic acid encoding for Nigiri was cloned into an E. coli recombination reporter plasmid that comprised two nox-sites of the same orientation. A plasmid containing gene coding for Panto protein and two identical sequences of pox site was created in a similar way. The recombination reporter plasmid was based on the plasmid pEVO (Buchholz and Stewart, 2001), in which the recombinase was inserted via a BsrGI and XbaI cleavage site. In the plasmid, the two vox-sites flanked an approximately 1 kb DNA segment that was excised by DNA-recombination (FIG. 12). DNA recombination was induced by the addition of L (+)-arabinose. It was shown that Vika mediated a DNA recombination at pox-sites Panto and Nigri on nox sites. Therefore, it could be shown that the Panto/pox and Nigri/nox system are recombinase systems applicable in E. coli cells.

CITED NON-PATENT LITERATURE

Buchholz, F., and Bishop, J. (2001). loxP-directed cloning: Use Cre recombinase as a universal restriction enzyme. BioTechniques 31, 906-.
Buchholz, F., and Stewart, A. F. (2001). Alteration of Cre recombinase site specificity by substrate-linked protein evolution. Nat Biotechnol 19, 1047-1052.
Chung Y et al. Cell Stem Cell 2008 (2): 113-117, and supplemental material
Lin et al. Cell Res 2007; 17:999-1007
Mai et al. Cell Res 2007 17: 1008-1019
Suzuki, E., and Nakayama, M. (2011). VCre/VloxP and SCre/SloxP: new site-specific recombination systems for genome engineering. Nucleic Acids Research 39, e49-e49.

---

The invention claimed is:

1. A method for producing a site-specific DNA-recombination, comprising:
contacting a protein with recombinase activity inside a cell, wherein the protein has an amino acid sequence of at least 99% amino acid sequence identity to SEQ ID No. 37 with at least two recognition sites that are identical or reverse complementary to each other, wherein at least one recognition site comprises the nucleic acid sequence of SEQ ID No. 38 or reverse complementary thereto, wherein upon binding of the protein with recombinase activity to the two recognition sites site-specific DNA-recombination occurs.

2. The method according to claim 1, further comprising: introducing into the cell a nucleic acid encoding for the protein with recombinase activity.

3. The method according to claim 1, wherein the cell comprises a nucleic acid encoding for the protein with recombinase activity, wherein the nucleic acid encoding for the protein with recombinase activity comprises a regulatory nucleic acid sequence and expression of the nucleic acid encoding for the protein with recombinase activity is produced by activating the regulatory nucleic acid sequence.

4. The method according to claim 1, wherein the cell is selected from eukaryotic or bacterial cells.

5. A vector comprising at least one identical nucleic acid having the sequence of SEQ ID NO: 38 or a nucleic acid sequence reverse complementary thereto, wherein the vector is a plasmid, virus, or artificial chromosome.

6. A method for producing a site-specific DNA recombination comprising: contacting the vector of claim 5 with a cell, wherein the vector comprises a nucleic acid encoding a protein with recombinase activity, wherein the protein comprises an amino acid sequence having at least 99% amino acid sequence identity to SEQ ID No. 37, wherein upon binding of the protein with the vector, site-specific DNA-recombination occurs.

7. The method according to claim 6, further comprising introducing into the cell a nucleic acid encoding for a protein with recombinase activity.

8. An isolated host cell or non-human host organism, comprising:
   (a) a recombinant DNA fragment comprising at least one nucleic acid having the sequence of SEQ ID NO: 38 or a nucleic acid sequence reverse complementary to SEQ ID NO: 38, or
   (b) a recombinant DNA fragment comprising a vector according to claim 5; and/or a vector comprising a nucleic acid encoding for a protein with recombinase activity wherein the protein comprises an amino acid sequence having at least 99% amino acid sequence identity with SEQ ID NO: 37.

* * * * *